(12) United States Patent
Fefer et al.

(10) Patent No.: US 9,826,738 B2
(45) Date of Patent: *Nov. 28, 2017

(54) TURFGRASS FUNGICIDE FORMULATION WITH PIGMENT

(71) Applicant: Suncor Energy Inc., Calgary (CA)

(72) Inventors: Michael Fefer, Whitby (CA); Jun Liu, Oakville (CA); Tomoki Ruo, Oakville (CA); Sonia Edith Hevia, Mississauga (CA)

(73) Assignee: Suncor Energy Inc., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,147

(22) Filed: Sep. 21, 2016

(65) Prior Publication Data

US 2017/0071201 A1 Mar. 16, 2017

Related U.S. Application Data

(63) Continuation of application No. 14/481,312, filed on Sep. 9, 2014, now Pat. No. 9,485,988, which is a continuation of application No. 13/832,808, filed on Mar. 15, 2013, now Pat. No. 8,853,128, which is a continuation of application No. 12/492,863, filed on Jun. 26, 2009, now Pat. No. 8,569,210.

(60) Provisional application No. 61/147,523, filed on Jan. 27, 2009, provisional application No. 61/075,821, filed on Jun. 26, 2008.

(51) Int. Cl.
| | |
|---|---|
| *A01N 25/30* | (2006.01) |
| *A01N 59/20* | (2006.01) |
| *A01N 55/02* | (2006.01) |
| *A01N 25/00* | (2006.01) |
| *A61K 31/155* | (2006.01) |
| *A01N 37/34* | (2006.01) |
| *A01N 43/90* | (2006.01) |
| *C09B 67/20* | (2006.01) |
| *C09B 67/46* | (2006.01) |
| *A01N 43/52* | (2006.01) |
| *A01N 27/00* | (2006.01) |
| *A01N 43/653* | (2006.01) |
| *A01N 47/30* | (2006.01) |
| *A01N 47/38* | (2006.01) |
| *A01N 47/40* | (2006.01) |
| *A01N 25/04* | (2006.01) |

(52) U.S. Cl.
CPC ............ *A01N 37/34* (2013.01); *A01N 25/00* (2013.01); *A01N 25/04* (2013.01); *A01N 25/30* (2013.01); *A01N 27/00* (2013.01); *A01N 43/52* (2013.01); *A01N 43/653* (2013.01); *A01N 43/90* (2013.01); *A01N 47/30* (2013.01); *A01N 47/38* (2013.01); *A01N 47/40* (2013.01); *A01N 55/02* (2013.01); *C09B 67/0067* (2013.01); *C09B 67/0089* (2013.01)

(58) Field of Classification Search
None
See application file for complete search history.

(56) References Cited

U.S. PATENT DOCUMENTS

| | | |
|---|---|---|
| 2,714,062 A | 7/1955 | Lockrey et al. |
| 2,786,821 A | 3/1957 | Gardner et al. |
| 2,870,037 A | 1/1959 | Converse et al. |
| 3,113,066 A | 12/1963 | Edmond |
| 3,131,119 A | 4/1964 | Fordyce et al. |
| 3,426,126 A | 2/1969 | Thome et al. |
| 3,615,799 A | 10/1971 | Gannon et al. |
| 3,689,574 A | 9/1972 | Engelhart |
| 3,799,758 A | 3/1974 | Franz |
| 3,948,635 A | 4/1976 | Vachette et al. |
| 3,950,265 A | 4/1976 | Albrecht et al. |
| 3,997,322 A | 12/1976 | Ratledge |
| 4,002,628 A | 1/1977 | Benefiel |
| 4,015,970 A | 4/1977 | Hennart |
| 4,041,164 A | 8/1977 | Albrecht et al. |
| 4,094,845 A | 6/1978 | De Long |

(Continued)

FOREIGN PATENT DOCUMENTS

| | | |
|---|---|---|
| CA | 964482 | 3/1975 |
| CA | 2069311 | 4/1991 |

(Continued)

OTHER PUBLICATIONS

"Addendum 9. Northeastern Collegiate Weed Science Contest Weed, Crop, and Herbicide Lists," revised May 2007. Retrieved from the Internet: <URL: http://www.newss.org/docs/mop/addendum-9.pdf>, 7 pages.

(Continued)

*Primary Examiner* — Abigail Vanhorn
(74) *Attorney, Agent, or Firm* — Fish & Richardson P.C.

(57) ABSTRACT

Oil-in-water fungicidal formulations are prepared having pigment dispersed therein, the pigment being stable within the oil-in-water emulsion as a result of the addition of suitable silicone surfactants and suitable emulsifiers. The formulations can be prepared either as a 2-pack formulation or as a single formulation. In the case of the single formulation polyethylene glycol is also added. In either case, the formulations show a synergistic effect through the addition of the pigment, the resulting formulations having an increased efficacy. Further, the formulations show a synergistic effect when mixed with conventional chemical fungicides, both being added in reduced amounts compared to recommended rates.

27 Claims, 17 Drawing Sheets

(56) References Cited

U.S. PATENT DOCUMENTS

| | | |
|---|---|---|
| 4,124,720 A | 11/1978 | Wenmaekers |
| 4,243,405 A | 1/1981 | Balasubramanyan et al. |
| 4,431,554 A | 2/1984 | Baur |
| 4,584,013 A | 4/1986 | Brunner |
| 4,618,360 A | 10/1986 | Brunner |
| 4,693,745 A | 9/1987 | Brunner |
| 4,698,334 A | 10/1987 | Horriere et al. |
| 4,734,432 A | 3/1988 | Szego et al. |
| 4,737,515 A | 4/1988 | Hallenbach et al. |
| 4,761,423 A | 8/1988 | Szego et al. |
| 4,826,863 A | 5/1989 | Szego et al. |
| 4,834,908 A | 5/1989 | Hazen et al. |
| 4,853,026 A | 8/1989 | Frisch et al. |
| 4,902,333 A | 2/1990 | Quimby, Jr. |
| 4,971,840 A | 11/1990 | Boho et al. |
| 5,084,087 A | 1/1992 | Hazen et al. |
| 5,102,442 A | 4/1992 | Hazen et al. |
| 5,137,726 A | 8/1992 | Ogawa |
| 5,178,795 A | 1/1993 | Roberts |
| 5,185,151 A | 2/1993 | Young |
| 5,206,021 A | 4/1993 | Dookhith |
| 5,229,356 A | 7/1993 | Tocker |
| 5,238,604 A | 8/1993 | Hazen et al. |
| 5,308,827 A | 5/1994 | Sakamoto et al. |
| 5,330,995 A | 7/1994 | Eicken et al. |
| 5,336,661 A | 8/1994 | Lucas |
| 5,352,729 A | 10/1994 | Birkhofer et al. |
| 5,362,167 A | 11/1994 | Loftin |
| 5,393,770 A | 2/1995 | Grayson |
| 5,393,791 A | 2/1995 | Roberts |
| 5,409,885 A | 4/1995 | Derian et al. |
| 5,504,054 A | 4/1996 | Murphy |
| 5,547,918 A | 8/1996 | Newton et al. |
| 5,558,806 A | 9/1996 | Policello et al. |
| 5,580,567 A | 12/1996 | Roberts |
| 5,599,768 A | 2/1997 | Hermansky |
| 5,599,804 A | 2/1997 | Mudge |
| 5,614,203 A | 3/1997 | Dezur |
| 5,643,852 A | 7/1997 | Lucas et al. |
| 5,658,851 A | 8/1997 | Murphy et al. |
| 5,665,672 A | 9/1997 | Lucas |
| 5,668,086 A | 9/1997 | Tadayuki et al. |
| 5,703,016 A | 12/1997 | Magin et al. |
| 5,739,371 A | 4/1998 | O'Lenick, Jr. |
| 5,741,502 A | 4/1998 | Roberts |
| 5,919,858 A | 7/1999 | Loftin |
| 5,958,104 A | 9/1999 | Nonomura et al. |
| 5,989,331 A | 11/1999 | Bauer et al. |
| 6,033,647 A | 3/2000 | Touzan et al. |
| 6,117,820 A | 9/2000 | Cutler et al. |
| 6,146,652 A | 11/2000 | Gore et al. |
| 6,159,900 A | 12/2000 | Bieringer et al. |
| 6,162,763 A | 12/2000 | Tateno |
| 6,210,656 B1 | 4/2001 | Touzan et al. |
| 6,221,811 B1 | 4/2001 | Policello et al. |
| 6,329,321 B2 | 12/2001 | Okura et al. |
| 6,403,061 B1 | 6/2002 | Candau et al. |
| 6,416,748 B1 | 7/2002 | Candau et al. |
| 6,432,877 B2 | 8/2002 | Okura et al. |
| 6,515,031 B2 | 2/2003 | Fefer |
| 6,673,360 B2 | 1/2004 | Fefer |
| 6,683,030 B2 | 1/2004 | Kober et al. |
| 6,713,518 B1 | 3/2004 | Bessette et al. |
| 6,727,205 B2 | 4/2004 | Brinkman |
| 6,734,202 B2 | 5/2004 | Cotter et al. |
| 6,803,345 B2 | 10/2004 | Herold et al. |
| 6,878,674 B2 | 4/2005 | Kobayashi |
| 6,972,273 B2 | 12/2005 | Sedun et al. |
| 7,135,435 B2 | 11/2006 | Cooper et al. |
| 7,166,725 B2 | 1/2007 | Fang et al. |
| 7,799,343 B2 | 9/2010 | Loughner |
| 7,923,452 B2 | 4/2011 | Birner et al. |
| RE42,394 E | 5/2011 | Mudge |
| 8,076,267 B2 | 12/2011 | Diebold et al. |
| 8,298,990 B2 | 10/2012 | Wu et al. |
| 8,426,343 B2 | 4/2013 | Norton et al. |
| 8,569,210 B2 * | 10/2013 | Fefer ..................... A01N 43/90 424/405 |
| 8,747,874 B2 | 6/2014 | Fefer |
| 8,748,342 B2 | 6/2014 | Gewehr et al. |
| 8,853,128 B2 * | 10/2014 | Fefer ..................... A01N 43/90 424/405 |
| 9,044,008 B2 | 6/2015 | Fefer |
| 9,226,504 B2 * | 1/2016 | Fefer ..................... A01N 43/40 |
| 9,357,768 B2 | 6/2016 | Fefer et al. |
| 9,451,773 B2 | 9/2016 | Fefer et al. |
| 9,485,988 B2 * | 11/2016 | Fefer ..................... A01N 43/90 |
| 2001/0019728 A1 | 9/2001 | Basinger et al. |
| 2002/0161057 A1 | 10/2002 | Fefer |
| 2003/0087764 A1 | 5/2003 | Pallas et al. |
| 2003/0185754 A1 | 10/2003 | Cohen et al. |
| 2003/0187079 A1 | 10/2003 | Fefer |
| 2003/0194454 A1 | 10/2003 | Bessette et al. |
| 2003/0198659 A1 | 10/2003 | Hoffmann et al. |
| 2003/0198696 A1 | 10/2003 | Keen |
| 2004/0132621 A1 | 7/2004 | Frisch et al. |
| 2004/0151749 A1 | 8/2004 | Hasebe et al. |
| 2004/0167034 A1 | 8/2004 | Coote et al. |
| 2004/0192556 A1 | 9/2004 | Schregenberger et al. |
| 2005/0026786 A1 | 2/2005 | Deckwer et al. |
| 2005/0181949 A1 | 8/2005 | Norton et al. |
| 2005/0202102 A1 | 9/2005 | Miller |
| 2005/0233907 A1 | 10/2005 | Nabors et al. |
| 2005/0244357 A1 | 11/2005 | Sieverding |
| 2005/0261379 A1 | 11/2005 | Fefer |
| 2005/0274164 A1 | 12/2005 | Coates et al. |
| 2006/0063676 A1 | 3/2006 | Brigance et al. |
| 2006/0068991 A1 | 3/2006 | Norton et al. |
| 2006/0194699 A1 | 8/2006 | Moucharafieh et al. |
| 2006/0276339 A1 | 12/2006 | Windsor et al. |
| 2006/0282961 A1 | 12/2006 | Hughes |
| 2006/0293188 A1 | 12/2006 | Norton et al. |
| 2007/0184005 A1 | 8/2007 | Policello et al. |
| 2007/0197386 A1 | 8/2007 | Diebold et al. |
| 2007/0197387 A1 | 8/2007 | Polge |
| 2007/0287720 A1 | 12/2007 | Royalty et al. |
| 2008/0064601 A1 | 3/2008 | Casanello et al. |
| 2008/0085832 A1 | 4/2008 | Fefer et al. |
| 2008/0112909 A1 | 5/2008 | Faler et al. |
| 2008/0153702 A1 | 6/2008 | Voeste et al. |
| 2008/0161367 A1 | 7/2008 | Voeste et al. |
| 2008/0194704 A1 | 8/2008 | Bhatnagar et al. |
| 2008/0274888 A1 | 11/2008 | Goldstein |
| 2008/0280763 A1 | 11/2008 | Hodge et al. |
| 2008/0293567 A1 | 11/2008 | Birner et al. |
| 2009/0092986 A1 | 4/2009 | Taing et al. |
| 2009/0325922 A1 | 12/2009 | Fefer et al. |
| 2010/0016447 A1 | 1/2010 | Fefer |
| 2010/0099567 A1 | 4/2010 | Shinichi |
| 2010/0317527 A1 | 12/2010 | Takeuchi et al. |
| 2011/0275516 A1 | 11/2011 | Wu et al. |
| 2011/0306495 A1 | 12/2011 | Sanaraheewa et al. |
| 2012/0245232 A1 | 9/2012 | Bousque et al. |
| 2013/0253016 A1 | 9/2013 | Fefer et al. |
| 2013/0303374 A1 | 11/2013 | Fefer et al. |
| 2013/0324620 A1 | 12/2013 | Fefer |
| 2014/0107070 A1 | 4/2014 | Fefer et al. |
| 2014/0228218 A1 | 8/2014 | Fefer et al. |
| 2014/0256556 A1 | 9/2014 | Fefer et al. |
| 2015/0065475 A1 | 3/2015 | Fefer et al. |
| 2015/0237869 A1 | 8/2015 | Fefer |
| 2015/0305329 A1 | 10/2015 | Fefer |
| 2016/0150783 A1 | 6/2016 | Fefer et al. |
| 2016/0198723 A1 | 7/2016 | Fefer |
| 2016/0286801 A1 | 10/2016 | Liu et al. |

FOREIGN PATENT DOCUMENTS

| | | |
|---|---|---|
| CA | 2434848 | 8/2002 |
| CA | 2507482 | 5/2005 |
| CA | 2496142 | 8/2005 |
| CA | 2472806 | 11/2005 |
| CA | 2568817 | 12/2005 |
| CA | 2209920 | 1/2007 |

(56) References Cited

FOREIGN PATENT DOCUMENTS

| | | |
|---|---|---|
| CA | 2562718 | 4/2008 |
| CA | 2605092 | 4/2008 |
| CA | 2625415 | 9/2008 |
| CA | 2711660 | 7/2009 |
| CA | 2748084 | 7/2010 |
| CA | 2839775 | 6/2013 |
| CN | 101238820 | 8/2008 |
| CN | 101304658 | 11/2008 |
| CN | 101390517 | 3/2009 |
| CN | 101415327 | 4/2009 |
| CN | 101473849 | 7/2009 |
| CN | 101998827 | 3/2011 |
| CN | 102215692 | 10/2011 |
| CN | 101773113 | 2/2013 |
| CN | 103732071 | 4/2014 |
| CN | 103763929 | 4/2014 |
| DE | 2511077 | 9/1976 |
| EP | 0267778 | 5/1988 |
| EP | 0498231 | 8/1992 |
| EP | 0526206 | 2/1993 |
| EP | 0598515 | 5/1994 |
| EP | 0862857 | 9/1998 |
| EP | 1173059 | 1/2002 |
| EP | 1563734 | 8/2005 |
| EP | 2319484 | 5/2011 |
| GB | 19295 | 0/1914 |
| GB | 191208748 | 4/1913 |
| GB | 745360 | 2/1956 |
| GB | 747909 | 4/1956 |
| GB | 748422 | 5/1956 |
| GB | 753976 | 8/1956 |
| GB | 758926 | 10/1956 |
| GB | 762866 | 12/1956 |
| GB | 763246 | 12/1956 |
| GB | 765459 | 1/1957 |
| GB | 792045 | 3/1958 |
| GB | 1044895 | 10/1966 |
| GB | 1168913 | 10/1969 |
| GB | 1249674 | 10/1971 |
| GB | 1417364 | 12/1975 |
| GB | 1499397 | 2/1978 |
| GB | 2123819 | 2/1984 |
| GB | 2176493 | 12/1986 |
| JP | 50-063141 | 5/1975 |
| JP | 54-036205 | 11/1979 |
| JP | 55-129213 | 10/1980 |
| JP | 57-028184 | 2/1982 |
| JP | 59-067205 | 4/1984 |
| JP | 59-210007 | 11/1984 |
| JP | 240601 | 10/1987 |
| JP | 2-138376 | 5/1990 |
| JP | 3-183505 | 8/1991 |
| JP | 3-221576 | 9/1991 |
| JP | 4-128003 | 4/1992 |
| JP | 07-179306 | 7/1995 |
| JP | 8-218225 | 8/1996 |
| JP | 10-029901 | 2/1998 |
| JP | 11-137084 | 5/1999 |
| JP | 11-349588 | 12/1999 |
| JP | 2006-124337 | 5/2006 |
| JP | 2008-502640 | 1/2008 |
| NL | 8900381 | 9/1990 |
| SU | 1021415 | 6/1983 |
| WO | WO 9007272 | 7/1990 |
| WO | WO 9312175 | 6/1993 |
| WO | WO 9621353 | 7/1996 |
| WO | WO 9632010 | 10/1996 |
| WO | WO 9632011 | 10/1996 |
| WO | WO 9835561 | 8/1998 |
| WO | WO 0064257 | 11/2000 |
| WO | WO 0221913 | 3/2002 |
| WO | WO 0234047 | 5/2002 |
| WO | WO 02089573 | 11/2002 |
| WO | WO 02096199 | 12/2002 |
| WO | WO 03047558 | 6/2003 |
| WO | WO 03101195 | 12/2003 |
| WO | WO 03105587 | 12/2003 |
| WO | WO 2004030641 | 4/2004 |
| WO | WO 2004080177 | 9/2004 |
| WO | WO 2005009132 | 2/2005 |
| WO | WO 2005018324 | 3/2005 |
| WO | WO 2005055716 | 6/2005 |
| WO | WO 2005082137 | 9/2005 |
| WO | WO 2006126211 | 11/2006 |
| WO | WO 2007054473 | 3/2007 |
| WO | WO 2007117720 | 10/2007 |
| WO | WO 2007136597 | 11/2007 |
| WO | WO 2008020872 | 2/2008 |
| WO | WO 2008030753 | 3/2008 |
| WO | WO 2008049192 | 5/2008 |
| WO | WO 2008069990 | 6/2008 |
| WO | WO 2008073397 | 6/2008 |
| WO | WO 2009080428 | 7/2009 |
| WO | WO 2009090181 | 7/2009 |
| WO | WO 2009098223 | 8/2009 |
| WO | WO 2009126370 | 10/2009 |
| WO | WO 2009139106 | 11/2009 |
| WO | WO 2009155693 | 12/2009 |
| WO | WO 2010043447 | 4/2010 |
| WO | WO 2010047185 | 4/2010 |
| WO | WO 2010132169 | 11/2010 |
| WO | WO 2011028987 | 3/2011 |
| WO | WO 2011070503 | 6/2011 |
| WO | WO 2012031355 | 3/2012 |
| WO | WO 2012040804 | 4/2012 |
| WO | WO 2012055991 | 5/2012 |
| WO | WO 2012126094 | 9/2012 |
| WO | WO 2012162844 | 12/2012 |
| WO | WO 2012162846 | 12/2012 |
| WO | WO 2012171126 | 12/2012 |
| WO | WO 2013078546 | 6/2013 |
| WO | WO 2014139012 | 9/2014 |

OTHER PUBLICATIONS

"An Online Guide to Plant Disease Control," Oregon State University Extension, print 1954, web 1996. Retrieved from the Internet: <URL: http:/plant-disease.orst.edu/>, 7 pages.

"Auxin," Wikipedia [online]. Retrieved from the Internet: <URL: http://en.wikipedia.org/wiki/Auxin>, 12 pages, Retrieved on Apr. 9, 2015.

"Bentgrass Dead Spot: Ophiosphaerella agrostis," Cornell University, created Apr. 2001, updated Jan. 2015. Retrieved from the Internet: <URL: http://plantclinic.cornell.edu/factsheets/bentgrassdeadspot.pdf>, 2 pages.

"Biological/Biorational Products for Disease Management," University of Connecticut Integrated Pest Management, [online] Jan. 2006. Retrieved from the Internet: <URL: http://www.ipm.uconn.edu/ipm/greenhs/htms/biofung.htm>, 6 pages.

"Characteristics of Plant Growth Regulators used in Fine Turf," Clemson University, retrieved on Aug. 24, 2011. Retrieved from the Internet: <URL: http://www.clemson.edu/extension/horticulture/turf/pest-guidelines/2011-p-est-guidelines/plantgrowth-reg-2011.pdf>, 9 pages.

"Chemical Update: Plant growth regulators," Grounds Maintenance [online] 2008. Retrieved from the Internet: <URL: http://www.grounds-mag.com/mag/grounds_maintenance_chemical_update_plant_6>, 2 pages.

"Civitas Technical Bulletin—Fungicide Resistance," Petro-Canada. Retrieved from the Internet: <URL: http://www.civitasturf.com/pdf/techBulletin.pdf>, 2 pages, 2009.

"Deformulation of RD 7212 Grazz Greenzit," 5 pages, 2009.

"Dollar Spot on Turfgrass," Cornell University, Retrieved on Aug. 22, 2011. Retrieved from the Internet: <URL: http://counties.cce.cornell.edu/wyoming/agriculture/resources/ipd/dollar_spot_turfgrass.htm>, 3 pages.

European Communication Pursuant to Article 94(3) EPC for European Application No. 14763572.6, dated Feb. 16, 2017, 8 pages.

"Emerald® Fungicide A Better Standard for Dollar Spot Control," Jan. 1, 2007 [retrieved on Jan. 14, 2014]. Retrieved from the Internet <URL: http://betterturf.basf.us/products/related-documents/emerald-info-sheet.pdf>, 2 pages.

(56) References Cited

OTHER PUBLICATIONS

"Food, Crop & Livestock Safety: Phytotoxicity," British Columbia Ministry of Agriculture. Archived Oct. 27, 2005. Retrieved from the Internet: <URL: http://www.agf.gov.bc.ca/pesticides/e_10.htm>, 2 pages.
"Fungicide Synergy," Kansas State University, Feb. 26, 2009. Retrieved from the Internet: <URL: http://www.ksuturf.com/LISTServArchive/2009-02-26-Fungicide-Synergy.pdf>, 3 pages.
"Gray leaf spot of perennial ryegrass," Kansas State University Turfgrass Research, 4 pages, revised Aug. 2008.
"Heat Stress Study Using Greenzit Pigment," University of Guelph, 3 pages, 2009.
"Herbicide Recommendations for Turfgrass: Postemergence Broadleaf Herbicides," Ontario Ministry of Agriculture, Food and Rural Affairs, Nov. 25, 2002, reviewed May 15, 2006. Retrieved from the Internet: <URL: http://www.omafra.gov.on.ca/english/crops/pub75/17turpbh.htm>, 7 pages.
"Herbicide," Wikipedia [online], retrieved on Aug. 29, 2006. Retrieved from the Internet: <http://en.wikipedia.org/wiki/Herbicide>, 5 pages.
"Horticultural Oils," IPM of Alaska [online] retrieved on Apr. 5, 2005. Retrieved from the Internet: <URL: http:/www.ipmofalaska.com/filed/hortoils.html>, 3 pages.
"Inert (other) Pesticide Ingredients in Pesticide Products," U.S. Environment Protection Agency, retrieved Sep. 11, 2007. Retrieved from the Internet: <http://www.epa.gov/opprd001/inerts/lists.html> 3 pages.
"It pays to be pure," Retrieved from the Internet: <http://www.findarticles.com/p/articles/mi-qa3824/is-200405/ai-n9424665/print>, Meister Media Worldwide, 1 pages, May 2004.
"Kannar Product Range Turf Enhancing Products," 1 page. Retrieved on Dec. 14, 2007. Retrieved from the Internet: <URL: http://web.archive.org/web/20040101182326/http:kannar.com/>, 1 page.
"Leaf Spot and Melting-out (crown and root rot) Diseases," Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/leaf-spot>, 2 pages.
"Performance of generic phosphite fungicides: A status report," AgNet Mar. 8, 2004, The Canadian Phytopathological Society, Retrieved from the Internet: <URL: http://www.cps-scp.ca/pathologynews/performanceofgenericfungicides.html>, 2 pages.
"Plant Growth Regulators for Turf, Landscape and Garden," Lawn Care Academy [online], retrieved Dec. 28, 2010. Retrieved from the Internet: <URL: http://www.lawn-care-academy.com/plant-growth-regulators.html>, 6 pages.
"The National Turfgrass Research Initiative: Enhancing America's Beauty Protecting America's Natural Resources Ensuring the Health and Safety of all Americans," Retrieved from the Internet: <URL: http://www.ntep.org/pdf/turfinitiative.pdf>, Apr. 2003, 22 pages.
"The Stylet-Oil User's Guide," Retrieved from the Internet: <URL: http://www.stylet-oil.com>, 15 pages. Retrieved on Mar. 22, 2005.
"Trinexapac-ethyl—Compound Summary," PubChem Public Chemical Database, [online] retrieved on Aug. 25, 2011. Retrieved from the Internet: <URL: http://pubchem.ncbi.nlm.nih.gov/summary/summary.cgi?cid=92421&loc=ec_rcs>, 3 pages.
"Turf grass coloration using hexadentate cobalt phthalocyanine amine complex salts," AN-1976-74211X[40], p. 1, 1975.
"Turfgrass Diseases: Leaf Spots and Tip Blights, Melting Out, Crown and Root Rots," University of Rhode Island Landscape Horticulture Program, 2000. Retrieved from the Internet: <URL: http://www.uri.edu/ce/factsheets/prints/leafspotsetcprint.html>, 3 pages.
"Turfgrass Pest Management Manual: A Guide to Major Turfgrass Pests & Turfgrasses," North Carolina State University, Mar. 26, 2007. Retrieved from the Internet: <URL: http://www.turffiles.ncsu. edu/PDFFiles/004041/Turfgrass_Pest_Management_Manual_A_Guide_to_Major_Turfgrass_Pests_and_Turfgrasses.pdf>, 106 pages.
Aerosil 200, Evonik [online] <URL: http://www.aerosil.com/lpa-productfinder/page/productsbytext/detail.html?pid=1855&lang=en>, Jun. 19, 2012, 1 page.
Agnello, "Petroleum-derived spray oils: chemistry, history, refining and formulation," in Beattie, G.A.C., Watson, D.M., Stevens, M., Spooner-Hart, R. and Rae, D.J. (eds). Splay Oils Beyond 2000—Sustainable Pest & Disease Management. University of Western Sydney, 2002. Retrieved from the Internet: <URL: http://web.entomology.cornell.edu/agnello/assets/1-1_Agnello.pdf>, 17 pages.
Bakke, "Analysis of Issues Surrounding the Use of Spray Adjuvants with Herbicides," Dec. 2002, Revised Jan. 2007. Retrieved from the Internet: <URL: http://www.fs.usda.gov/Internet/FSE_DOCUMENTS/fsbdev3_045552.pdf>, 61 pages.
Beasley and Branham, "Trinexapac-ethyl and Paclobutrazol Affect Kentucky Bluegrass Single-Leaf Carbon Exchange Rates and Plant Growth," *Crop Sci.*, 47:132-138, Jan. 22, 2007.
Beckerman, "Disease Management Strategies for Horticultural Crops: Using Organic Fungicides," Purdue Extension, Apr. 1, 2008 [retrieved on Sep. 29, 2014]. Retrieved from the Internet: <URL: https://www.extension.purdue.edu/extmedia/bp/bp-69-w.pdf>, 4 pages.
Bell et al., "Comparison of Turfgrass Visual Quality Ratings with Ratings Determined Using a Handheld Optical Sensor," *Hortitechnology.*, 19(2):309-316, 2009.
Ben-Tal, "Effect of Chloro-Aluminum-Phtahalocyanine on the Growth of Lenma gibba G3" *J. Plant. Physiol.*, 135(5):635-636, 1989.
Beresford, "DMI (demethylation inhibitor) management strategy," *Prevention and management strategies.*, pp. 21-25, 2003.
Bigelow et al., "Evaluation of Commercially Available Plant Growth Regulator Programs for Creeping Bentgrass Fairway Management," Retrieved from the Internet: <URL: http://www.agry.purdue.edu/turf/report/2003/Page66.pdf>, pp. 66-74, 2003.
Biology and Control of Dollar Spot Disease, Ontario Ministry of Agriculture Food & Rural Affairs, Retrieved on Aug. 22, 2011. Retrieved from the Internet: <URL: http://www.omafra.gov.on.ca/english/crops/facts/info_turfdollarspot.htm>, 3 pages.
Blenis et al, "Evaluation of Fungicides and Surfactants for Control of Fairy Rings Caused by Marasmius oreades (Bolt ex. Fr.) Fr.," *HortScience* 32(6):1077-1084, 1997.
Bradley, "Some ways in which a paraffin oil impedes APHID transmission of potato virus Y," *Canadian Journal of Microbiology*, 9(3): 369-380, 1963.
Bremer et al., "Relationships between Normalized Difference Vegetation Index and Visual Quality in Cool-Season Turfgrass: I. Variation among Species and Cultivars," *Crop Science.* 51:2212-2218, 2011.
Brochure for Civitas, Petro-Canada, retrieved on Aug. 22, 2011. Retrieved from the Internet <URL: http://www.civitasturf.com/pdf/CIVITAS-technical-brochure.pdf>, 12 pages.
Brown Patch on Turfgrass *Rhizoctonia spp.*, Cornell University Department of Plant Pathology and Plant-Microbe Biology, created Aug. 1999, updated May 2011. Retrieved from the Internet: <URL: http://plantclinic.cornell.edu/factsheets/brownpatch.pdf>, 3 pages.
Brown Patch Rhizoctonia solani, University of Guelph, Nov. 27, 2003. Retrieved from the Internet: <URL: http://www.uoguelph.ca/pdc/Factsheets/PDFs/127TurfBrownPatch.pdf>, 1 page.
Brown Patch, Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/brown- -patch>, 3 pages.
Buckley et al., "An Integrated Approach to Insect Management in Turfgrass: Black Cutworm," Rutgers, The State University of New Jersey, Mar. 2010. Retrieved from the Internet: <URL: http://snyderfarm.rutgers.edu/pdfs/BlackCutworms.pdf>, 3 pages.
Bunderson et al., "Tools for Evaluating Native Grasses as Low Maintenance Turf," *Hortitechnology.*, 19(3):626-632, 2009.
Burpee and Latin, "Reassessment of Fungicide Synergism for Control of Dollar Spot," *Plant Disease* 92(4):601-606, 2008.

(56) References Cited

OTHER PUBLICATIONS

Burpee et al., "Interactive Effects of Plant Growth Regulators and Fungicides on Epidemics of Dollar Spot in Creeping Bentgrass," *Plant Disease*, 80(11):1245-1250, 1996.
Burr and Warren, "Enhancement of Herbicide Activitiy with an Isoparaffinic Oil Carrier," *Weed Science*, 19(6):701-705, Nov. 1971.
Burt, "Tolerance of warmseason turf grasses to herbicides," Plantation Field Laboratory Mimeo Report PFL66-1, University of Florida Digital Collections [online] Aug. 1966. Retrieved from the Internet: <URL: http://ufdc.ufl.edu//UF00076427/00001>, 11 pages.
Buss, "Insect Pest Management on Golf Courses," University of Florida. Retrieved from the Internet: <URL: http://edis.ifas.ufl.edu/in410>, 14 pages. Retrieved on Aug. 26, 2011.
Buss, "Insect Pest Management on Turfgrass," University of Florida. Retrieved from the Internet: <URL: http://edis.ifas.ufl.edu/ig001>, 13 pages. Retrieved on Aug. 26, 2011.
Butler, "Cultural practices and their effects upon turf grass growth and stress tolerance," The British and International Golf Greenkeepers Association Limited, Jul. 2006. Retrieved from the Internet: <URL: http://www.bigga.org.uk/about-us/magazine/back-issues/07-2006/cultural-pray-tim-butler/00919.html>, 7 pages.
Bywater, "Plant Growth Regulators: Mode of Action," AGCSA [online] Australian Turfgrass Management vol. 3.3, Jun.-Jul. 2001. Retrieved from the Internet: <URL: http://www.agcsa.com.au/static/atm_articles/html/3_3c.html>, 3 pages.
CAS No. 117428-22-5, picoxystrobin, methyl (2E)-3-methoxy-2-{2-[6-(thfluoromethyl)-2-pyridyloxymethyl]phenyl}acrylate; methyl (2E)-3-methoxy-2-[2-({[6-(trifluoromethyl)pyridin-2-yl]oxy}methyl)phenyl]prop-2-enoate; (E)-Methyl 3-methoxy-2-(2-(((6-(trifluoromethyl)pyridin 2-yl)oxy)methyl)phenyl)acrylate; ACANTO; methyl (αE)-α-(methoxymethylene)-2-[[[6-(trifluoromethyl)-2-pyridinyl]oxy]methyl]benzeneacetate; Picoxystrobin; ZA1963; © 2013-2016, retrieved Nov. 28, 2016, http://www.molbase.com/en/precursor_117428-22-5-moldata-29033.html?synonyms=1, 1 page.
CAS No. 131807-57-3, (RS)-3-anilino-5-methyl-5-(4-phenoxyphenyl)-1,3-oxazolidine-2,4-dione; Famoxate; DPX-JE 874; 3-anilino-5-methyl-5-(4-phenoxyphenyl)-1,3 oxazolidine-2,4-dione; Famoxadone; 3-Anilino-5-methyl-5-(4 phenoxyphenyl)oxazolidine-2,4-dione; 5-methyl-5-(4-phenoxyphenyl)-3-(phenylamino)-2,4-oxazolidinedione; rac-(5R)-3-anilino-5-methyl-5-(4-phenoxyphenyl)-1,3-oxazolidine-2,4-dione; © 2013-2016, retrieved on Nov. 17, 2016, http://molbase.com/en/precursor_131807-57-3-moldata-3366.html?synonyms=1, 1 page.
CAS No. 133408-50-1, (E)-METOMINOSTROBIN; (2E)-2-(methoxyimino)-N-methyl-2-(2-phenoxyphenyl)acetamide; Metominofen; (E)-2-(methoxylinino)-N-methyl-2-(2-phenoxyphenyl)acetamide; Metominostrobin; ssf-126; (αE)-α-(methoxyimino)-N-methyl-2 phenoxybenzeneacetamide; metaminostrobin; © 2013-2016, retrieved on Nov. 28, 2016, http://www.molbase.com/en/precursor_133408-50-1-moldata-473468.html?synonyms=1, 1 page.
CAS No. 143390-89-0, methyl (αE)-α-(methoxyimino)-2-[(2-methylphenoxy)methyl]benzeneacetate; methyl (2E)-2-methoxyimino-2-[2-[(2-methylphenoxy)methyl]phenyl]acetate; Kresoxim-methyl; methyl (E)-methoxyimino[α-(o-tolyloxy)-o-tolyl]acetate; methyl (2E)-(methoxyimino){[(2-methylphenoxy)methyl]phenyl}acetate; © 2013-2016 , retrieved on Nov. 28, 2016, http://www.molbase.com/en/precursor_143390-89-0-moldata-28515.html?synonyms=1, 1 page.
CAS No. 161326-34-7, (S)-1-Anilino-4-methyl-2-methylthio-4-phenyl-2-imidazolin-5-one; (5S)-3-anilino-5-methyl-2-methylsulfanyl-5-phenylimidazol-4-one; Fenamidone; (5S)-3-anilino-5-methyl-2-(methylsulfanyl)-5-phenyl-3,5-dihydro-4H-imidazol-4-one; (5S)-3,5-dihydro-5-methyl-2-(methylthio)-5-phenyl-3-(phenylamino)-4H-imidazol-4-one; (S)-1-anilino-4-methyl-2-methylthio-4-phenylimidazolin-5-one; © 2013-2016, retrieved on Nov. 17, 2016, http://www.molbase.com/en/precursor_161326-34-7-moldata-475051.html?synonyms=1, 1 page.
CAS No. 248593-16-0, (2E)-2-[2-[[(E)-[(3E,4E)-3,4-bis(methoxyimino)pentan-2-ylidene]amino]oxymethyl]phenyl]-2-methoxyimino-N-methylacetamide; (2E)-2-(methoxyimino)-2-{2-[(3E,5E,6E)-5-(methoxyimino)-4,6-dimethyl-2,8-dioxa-3,7-diazamona-3,6-dien-1 yl]phenyl}-N-methylacetamide; Orysastrobin [ISO]; (αE)-α-(methoxyimino)-2-[(3E,5E,6E)-5-(methoxyimino)-4,6-dimethyl-2,8-dioxa-3,7-diaza-3,6-nonadienyl]-N-methylbenzeneacetamide; Orysastrobin; © 2013-2016, retrieved on Nov. 28, 2016, http://www.molbase.com/en/precursor_248593-16-0-moldata-1557223.html?synonyms=1, 1 page.
CAS No. 799247-52-2, pyribencarb; methyl {2-chloro-5-[(1E)-1-(6-methyl-2-pyridylmethoxyimino)ethyl]benzyl}carbamate; methyl [(2-chloro-5-{(1E)-N-[(6-methylpyridin-2-yl)methoxy]ethanimidoyl}phenyl)methyl]carbamate; methyl N-[[2-chloro-5-[(1E)-1-[[(6 methyl-2-pyridinyl)methoxy]imino]ethyl]phenyl]methyl]carbamate; methyl N-[[2-chloro-5-[(Z)-C-methyl-N-[(6-methylpyridin-2-yl)methoxy]carbonimidoyl]phenyl]methyl]carbamate; © 2013-2016, retrieved on Nov. 28, 2016, http://www.molbase.com/en/precursor_799247-52-2-moldata-1607308.html?synonyms=1, 1 page.
CAS No. 850881-70-8, "Coumoxystobin; Coumoxystrobine; methyl (2E)-2-(2-{[(3-butyl-4-methyl-2-oxo-2H-1-benzopyran-7-yl)oxy]methyl}phenyl)-3-methoxyprop-2-enoate; SYP 3375," © 2013-2016, retrieved on Nov. 17, 2016, http://www.molbase.com/en/850881-70-8-moldata-2475984.html, 1 page.
CAS No. 862588-11-2, Pyraoxystrobin; Benzeneacetic acid, 2-[[[3-(4-chlorophenyl)-1-methyl-1H-pyrazol-5-yl]oxy]methyl]-a-(methoxymethylene)-, methyl ester, (aE)—(CA Index Name), *STN*, entered STN on Sep. 7, 2005, retrieved on Nov. 28, 2016, stnc.cas.org, 3 pages.
Cawthon and Pyle, "Use of Plant Growth Regulators to Retard Growth of Bermudagrass and Dallisgrass in the Landscape," Texas A&M University, retrieved Aug. 24, 2011. Retrieved from the Internet: URL:<http://www.tamu-commerce.edu/agscience/res-dlc/turf/pgr.html>, 5 pages.
Chase and Simone, "Phytotoxicity on Foliage Ornamentals Caused by Bactericides and Fungicides," Plant Pathology Fact Sheet, Florida Cooperative Extension Service, Institute of Food and Agricultural Sciences, University of Florida. Retrieved from the Internet: <URL: http://plantpath.ifas.ufl.edultakextpublFactSheetsip-pOO30.pdf>, 8 pages. Retrieved on Aug. 26, 2011.
Chemical Structures, The Bugwood Network, Nov. 7, 2002. Retrieved from the Internet: <URL: http://www.bugwood.org/PAT/22chemicalstructures.html>, 8 pages.
Chen et al., "Rheological properties of silica particle suspensions in mineral oil," *J Dispers Sci Technol.*, 26(6):791-798, 2005.
Christians, "Creative uses for plant growth regulators," *USGA Green Sec. Rec*, 39: Sep. 11-13, 2001/ Oct. 2001.
Clarke et al., "Pest Control Recommendations for Lawn and Turf Areas, 2006" Rutgers NJAES Cooperative Extension, Jul. 13, 2006. Retrieved from the Internet: <URL: http://njaes.rutgers.edu/pubs/publication.asp?pid=e037>, 33 pages.
Cleary Chemical Corporation, "Use of Cleary's Grass Greenzit™," 1 page, 2004.
Cline, "OLR mating disruption just got easier," Western Farm Press [online] Jun. 1, 2001. Retrieved from the Internet: <URL: http://westernfarmpress.com/olr-mating-disruption-just-got-easier>, 4 pages.
Cockerham et al., "Evaluation of Turfgrass Growth Retardant Chemicals," *California Turfgrass Culture*, 23-24, 21(3):23-24, 1971.
Colby, "Calculating synergistic and antagonistic responses of herbicide combinations," *Weeds*, 20-22, 1967.
Coo-Ranger et al., "Ionic silicone surfactants in water-in-silicone oil emulsions containing proteins," *Polymer Preprints*, 45(1):674-675, 2004.
Cortes-Barco et al., "Comparison of induced resistance activated by benzothiadiazole,(2R, 3R)-butanediol and an isoparaffin mixture against anthracnose of Nicotiana benthamiana," *Plant pathology*, 59(4):643-653, 2010.

(56) References Cited

OTHER PUBLICATIONS

Cortes-Barco et al., "Induced systemic resistance against three foliar diseases of Agrostis stolonifera by (2R,3R)-butanediol or an isoparaffin mixture," *Annals of Applied Biology*, 157(2):179-189, 2010.
Corwin, "Integrated Pest Management: Identification & Management of Turfgrass Disease," University of Missouri Extension. Retrieved from the Internet: <URL: http://extension.missouri.edu/p/IPM1029> 56 pages, 2007.
Cranmer et al., "Controlled droplet application (CDA) of fluazifop and sethoxydim for annual and perennial weed control," 1983 Meeting of the Weed Science Society of America, 1983, 23-24, Weed Abstract vol. 033 Abs. (No. 00871).
Cranshaw, "Clover and Other Mites of Turfgrass," Colorado State University Extension. Dec. 2012. Retrieved from the Internet: <URL: http://www.ext.colostate.edu/pubs/insect/05505.html>, 2 pages.
Crocker & Simpson, "Pesticide screening test for the southern chinch bug," *Journal of Economic Entomology*, 74(6):730-731, 1981.
Croda, "Volpo," Croda Chemicals Europe Ltd, Jul. 2001. Retrieved from the Internet:<URL: http://www.chservice.ru/download/DC%20Volpo.pdf>, May 2004.
Derksen et al. (J Environ Hort. Mar. 2004 22(1):17-22).
Cropper, "Towards Reducing Fungicide Use in the Control of Dollar Spot (*Sclerotinia homoeocarpa* F.T. Bennett) Disease on Creeping Bentgrass (*Agrostis stolonifera* L.)," May 4, 2009, Master of Science Thesis, University of Kentucky. Retrieved from the Internet: <URL: http://archive.uky.edu/handle/10225/1044>, 69 pages.
Danneberger and Street, "Turfgrass Growth Substances," *Golf Course Management*, Apr. 1990, 58(4):80, 82, 86, 88.
Datapak for SALVO herbicide, United Agri Products Canada Inc., 14 pages, Oct. 2005.
Dell et al., "The Efficacy of JMS Stylet-Oil on Grape Powdery Mildew and Botrytis Bunch Rot and Effects on Fermentation," *Am. J. Enol. Vitic.*, 49(1):11-16, 1998.
Dickey, "Using plant growth regulators in turfgrass management (Green Science).," Golfscape [online] Sep. 1, 2002. Retrieved from the Internet: <URL: http://www.highbeam.com/doc/1G1-105617663.html/print>, 2 pages.
Diesburg, "Effects of Turf Colorants and FES04 on Spring Greenup of Zoysiagrass," 1990. Retrieved from the Internet: <URL: http://www.turf.uiuc.edu/research/summaries/1990/effect_colorant.pdf>, 2 pages.
Dokkuma, "Plant Growth Regulators as a Turfgrass Management Tool," Greenkeeper [online] 2008. Retrieved from the Internet: <URL: http://www.greenkeeper.com/upload/alinea_1425.pdf>, 4 pages.
Dokkuma, Plant Growth Regulators Used in Turfgrass Management, Greenkeeper [online] 2008. Retrieved from the Internet: <URL: http://www.greenkeeper.eu/upload/alinea_1420.pdf>, 4 pages.
Duell, "Turfgrass quality and phytotoxicity affected by growth retardants," Chapter 70. Retrieved from the Internet: <URL: http://archive.lib.msu.edu/tic/its/articles/1985pro749.pdf>, 8 pages. Retrieved on Aug. 24, 2011.
Engvild, "Herbicidal activity of 4-chloroindoleacetic acid and other auxins on pea, barley and mustard,"*Physiologia Plantarum*, 96(2):333-337, Feb. 1996.
Erhan and Nelsen, "Comparisons of volatile organic chemical content of news, sheetfed, and heatset ink formulations," *Journal of the American Oil Chemists' Society*, 78(4):419-422, 2001.
Fasold, "Plant Growth Regulators: More Color, Less Clippings," Irrigation and Green Industry [online], May 15, 2009. Retrieved from the Internet: <URL: http://www.igin.com/article-925-%20plant_growth_regulat.html>, 4 pages.
Fertilome, "Broad Spectrum Landscape & Garden Fungicide (32 oz)," Fertilome.com [online] archived on Dec. 30, 2010. Retrieved from the Internet: <URL: http://web.archive.org/web/20101230174658/http://www.fertilome.com/product.aspx?pid=9950d7c1-dfed-4268-9474-eb508f967dc0>, 2 pages.
Fidanza et al., "Evaluation of fungicide and plant growth regulator tank-mix programmes on dollar spot severity of creeping bentgrass," *Crop Protection*, 25(9):1032-1038, 2006.
Fidanza et al., "Use of a Soil Surfactant with Fungicides for Control of Fairy Ring Disease in Turfgrass," *Journal of ASTM International* 4(4):77-82, 2007.
Fishel, "Plant Growth Regulators," University of Florida, Feb. 2006, Revised Apr. 2009, 5 pages.
Fungicide Resistance Action Committee [FRAC] Code List: Fungicides sorted by mode of Action, Fungicide Resistance Action Committee, retrieved on Aug. 22, 2011. Retrieved from the Internet: <URL: http://www.frac.info/frac/publication/anhang/FRAC%20Code%20List%202011final.pdf>, 10 pages.
Furuta, "Strangers in a Strange Land," California Turfgrass Culture, 21(3):22-23, 1971.
Gaussoin and Branham, "Plant Growth Regulator Effects on Annual Bluegrass/Creeping Bentgrass Competition," Department of Crop & Soil Sciences Michigan State University, pp. 52-56, Jul. 2008. Retrieved from the Internet: <URL: http://archive.lib.msu.edu/tic/mitgc/article/198852a.pdf>.
Gauvrit and Cabanne, "Oils for weed control: Uses and mode of action," *Pesticide Science*, 37(2):147-153, 1993.
Gebhardt et al., "Herbicide application with the controlled droplet applicator when using soybean oil," American Society of Agricultural Engineers, Paper No. 83-1509, 13 pages, 1983.
Gilbert and Kopec, "Spring Greenup of Dormant Non-Overseeded Bermudagrass," University of Arizona College of Agriculture 2004 Turfgrass and Ornamental Research Report. Retrieved from the Internet: <URL: http://ag.arizona.edu/pubs/crops/az1359/az13593c11.pdf>, 4 pages.
Golden Artist Colors, "Pigment Identification Charts," Retrieved on Sep. 15, 2011. Retrieved from the Internet: <URL: http://www.goldenpaints.com/technicaldata/pigment.php>, 15 pages.
Goodwin and McBrydie, "Effect of surfactants on honey bee survival " *New Zealand Plant Protection*, 53:230-234, 2000.
Grey et al., "Timed Release of Flurprimidol from a Granular Formulation in Mulches and Sand," *HortScience*, 44(2):512-515, 2009.
Grover et al., "Droplet and Vapor Drift from Butyl Ester and Dimethylamine Salt of 2,4-D" *Weed Science*, 20(4): 320-324, Jul. 1972.
Guy et al., "The performance of postemergence grass herbicides applied with sprinkler irrigation," Proceedings of the 39th annual meeting of the Southern Weed Science Society, p. 106, 8A, 1986.
Harmon and Latin, "Gray leaf spot of perennial ryegrass," Plant Health Progress [online]. Retrieved from the Internet: <URL: http://www.plantmanagementnetwork.org/pub/php/diagnosticguide/2003/ryegrass/>, 8 pages, 2003.
Hartzler, "Role of spray adjuvants with postemergence herbicides," Iowa State University Weed Science [online], Mar. 7, 2001, Retrieved from the Internet: <URL: http:/www.weeds.iastate.edu/mgmt/2001/additives.htm>, 3 pages.
Heath et al., "Chelating agents and auxin," *Nature*, 201(4919):585-587, Feb. 8, 1964.
Heil and Bostock, "Induced systemic resistance (ISR) against pathogens in the context of induced plant defences," *Annals of Botany*, 89(5), 503-512, 2002.
Hill, "Silicone surfactants—new developments," *Current opinion in colloid & interface science*, 7(5):255-261, 2002.
Hodgson, "Armyworms and cutworms in turfgrass," Utah State University Extension, Jun. 2007. Retrieved from the Internet: <URL: http://utahpests.usu.edu/IPM/files/uploads/PDFDocs/factsheet-pdf/armyw-cutw-turf07.pdf>, 3 pages.
Hoffman et al., "Application of Fungicides for Suppression of Fusarium Head Blight (Scab)," North Dakota State University, May 2000. Retrieved from the Internet: <URL: http://www.ag.ndsu.edu/pubs/ageng/machine/ae1148.pdf>, 4 pages.
Hoffman, "Analysis of Alcohol and Alkylphenol Polyethers via Packed Column Supercritical Fluid Chromatography," (Doctoral dissertation, Virginia Polytechnic Institute and State University), 2004.

(56) References Cited

OTHER PUBLICATIONS

Holly Frontier®, "Sunspray Oils," 2014 [retrieved on Jul. 27, 2015]. Retrieved from the Internet: <URL: http://www.hollyfrontierlsp.com/Products/Horticultural-Oils/Sunspray-Oils/85/>, 1 page.
Horn, "Increasing the Effectiveness of Turf Herbicides by Use of Oil," Florida State Horticultural Society, pp. 499-509, 1966.
Horn, "Tolerance of Several Southern Turfgrasses to Various Spray Oils," Florida State Horticultural Society, pp. 494-499, 1966.
Hsiang et el. (Acta Silv. Lign. Hung. Spec. Edition (2007) 71-74).
Hsiang and Tian, "Chemical Trials for Dollar Spot Disease Control," Summer 2006, Guelph Turfgrass Institute, 2006 Annual Research Report, Retrieved from the Internet <URL: http://131.104.104.3/06anrep/40-42.pdf>, pp. 40-42.
Hsiang et al., "Baseline sensitivity and cross-resistance to demethylation-inhibiting fungicides in Ontario isolates of Sclerotinia homoeocarpa," *European journal of plant pathology*, 103(5):409-416, 1997.
Hsiang et al., "Sensitivity of Sclerotinia homoeocarpa to demethylation-inhibiting fungicides in Ontario, Canada, after a decade of use," *Plant pathology*, 56(3):500-507, 2007.
Huang, "Better Creeping Bentgrass Through Electricity," *GCM*, 2003, pp. 85-86. Retrieved from the Internet: <http://www2.gcsaa.org/gcm/2003/dec03/pdfs/12electricity.pdf>, 2 pages.
Huang, "Plant growth regulators: What and why," *Golf Course Management*, pp. 157-160, Jan. 2007.
Hwang et al., "The response of seeds and seedlings to treatment with indolylacetic acid" *Annals of Botany*, 4(13):31-37, Jan. 1, 1940.
Jordan, "Enhanced post-emergence herbicide efficacy with ultra-low volume application," Proceedingss of the 48th annual meeting of the Southern Weed Science Society, 48, pp. 208-212, 1995.
Kaminski and Dernoeden, "Dead Spot Disease of Creeping Bentgrass," University of Maryland, Nov. 2003. Retrieved from the Internet: <URL: http://www.hgic.umd.edu/content/documents/TT-14DeadSpot.pdf>, 2 pages.
Kaminski and Dernoeden, "Dead Spot of Creeping Bentgrass and Hybrid Bermudagrass," Plant Management Network [online], Apr. 19, 2005. Retrieved from the Internet: <URL: http://www.plantmanagementnetwork.org/pub/ats/diagnostic/2005/de-adspot/>, 8 pages.
Kaminski and Dernoeden, "Understanding Bentgrass Dead Spot," USGA Turfgrass and Environmental Research Online, 2(2):1-7, Jan. 15, 2003. Retrieved rom the Internet: <URL: http://turf.lib.msu.edu/tero/v02/n02.pdf>, 9 pages.
Kaminski, "Bentgrass dead spot," University of Connecticut, Dec. 2006. Retrieved from the Internet: <http://www.turf.uconn.edu/pdf/research/factsheets/Disease_Bentgrass_Dead_Spot.pdf>, 2 pages.
Knowles, D. A., "Formulation of Agrochemicals." Chemistry and Technology of Agrochemical Formulations. *Springer*., 41-79, 1998.
Kopec et al., "Repeat Applications of Paclobutrazole (TGR) Plant Growth Regulator on Overseeded Bermudagrass Turf: Weed Control and Bermudagrass Transition," Turfgrass, Landscape and Urban IPM Research Summary, The University of Arizona. Retrieved from the Internet: <URL: http://ag.arizona.edu/pubs/crops/az1487/14875e.pdf>, pp. 174-196, Feb. 2009.
Kopeck and Gilbert, "Overseed Greens Performance Trials," 6 pages, 1995-1996.
Koppenhofer et al., "An Integrated Approach to Insect Management in Turfgrass: Sod Webworms," Rutgers, The State University of New Jersey, Mar. 2010. Retrieved from the Internet: <URL: http://snyderfarm.rutgers.edu/pdfs/SodWebworms.pdf> 3 pages.
Koppenhofer et al., "An Integrated Approach to Insect Management in Turfgrass: White Grubs," Jun. 2002. Retrieved from the Internet: <URL: https://www.co.somerset.nj.us/pdf/JapBeetleFS.pdf>, 4 pages.
Kremer et al., "Control of Sclerotinia homoeocarpa in turfgrass using effective microorganisms," *EM World J*, 1:16-21, 2000.

Latin and Stewart, "Turfgrass Disease Profiles: Gray Leaf Spot," Purdue University. Retrieved from the Internet: <URL: https://www.extension.purdue.edu/extmedia/BP/BP-107-W.pdf> Apr. 2008, 2 pages.
Latin, "Turfgrass Disease Profiles: Brown Patch," Purdue University, Retrieved from the Internet: <URL: https://www.extension.purdue.edu/extmedia/BP/BP-106-W.pdf> Apr. 2008, 2 pages.
Latin, "Turfgrass Disease Profiles: Dollar Spot," Purdue University. Retrieved from the Internet: <URL: https://www.extension.purdue.edu/extmedia/BP/BP-105-W.pdf>, Jan. 2010, 3 pages.
Latin, "Turfgrass Disease Profiles: Gray Snow Mold," Purdue University, Retrieved from the Internet: <URL: https://www.extension.purdue.edu/extmedia/BP/BP-101-W.pdf> Jan. 2006, 3 pages.
Latin, "Turfgrass Disease Profiles: Leaf Spot/Melting Out," Purdue University, Retrieved from the Internet: <http://www.ces.purdue.edu/extmedia/bp/bp-103-w.pdf>, Apr. 2008, 2 pages.
Latin, "Turfgrass Disease Profiles: Pink Snow Mold and Microdochium Patch," Purdue University, Retrieved from the Internet: <URL: https://www.extension.purdue.edu/extmedia/BP/BP-102-W.pdf>, Jan. 2006, 3 pages.
Lickfeldt et al., "Implications of repeated trinexapac-ethyl applications on Kentucky bluegrass," *Agronomy Journal*, 93(5):1164-1168, 2001.
Lincoln County Noxious Weed Control, "Herbicide Facts," 2007, Retrieved from the Internet: <URL: http://www.co.lincoln.wa.us/WeedBoard/herbicide/herbicidefacts.pdf>, 22 pages.
Liu, "Cytokinin Effects on Creeping Bentgrass Responses to Heat Stress: I. Shoot and Root Growth," *Crop. Sci*., 42:457-465, 2002.
Liu, "Painting dormant bermudagrass putting greens," *Golf Course Manage*, 75(11):86-91, 2007.
Lopez et al., "Effect of indole-3-acetic acid, kinetin, and ethylenediaminetetraacetic acid on plant growth and uptake and translocation of lead, micronutrients, and macronutrients in alfalfa plants," *Int J Phytoremediation*., 11(2):131-149, Feb. 13, 2009.
Lorbeer, "Synergism, Antagonism, and Additive Action of Fungicides in Mixtures," *Phytopathology*, 86(11):1261-1262, 1996.
Material Safety Data Sheet for AGRI-DEX, Helena Chemical Company, 1 page, Apr. 29, 2005.
Material Safety Data Sheet for Banner MAXX, Syngenta Crop Protection, Inc., 5 pages, Aug. 30, 2010.
Material Safety Data Sheet for BLENDEX VHC, Helena Chemical Company, 1 page, Jul. 27, 2000.
Material Safety Data Sheet for Broadcoat Spray Adjuvant, Caltex Australia Limited, 5 pages, Sep. 2003.
Material Safety Data Sheet for Chipco Signature, Bayer CropScience Pty Ltd, May 1, 2007, 6 pages.
Material Safety Data Sheet for Chipco Signature, Bayer CropScience Pty Ltd, Oct. 21, 2002, 7 pages.
Material Safety Data Sheet for Civitas, Petro-Canada Lubricants, Inc., 6 pages, Mar. 21, 2011.
Material Safety Data Sheet for Cleary 3336 Plus, Cleary Chemical Corporation, Feb. 1, 2005, 4 pages.
Material Safety Data Sheet for Daconil 2787, Syngenta Crop Protection Canada, Inc., 7 pages, Dec. 31, 2008.
Material Safety Data Sheet for Daconil Ultrex Fungicide, Syngenta Crop Protection Canada, Inc., 7 pages, Aug. 1, 2009.
Material Safety Data Sheet for FORE 80 WP Rainshield, Dow AgroSciences, Jun. 1, 2001, 9 pages.
Material Safety Data Sheet for FORE Fungicide, Rohm and Haas Company, 9 pages, Oct. 16, 1995.
Material Safety Data Sheet for Grass Greenzit, W.A.Cleary Chemical Corporation, 2 pages, Oct. 1997.
Material Safety Data Sheet for Green Lawnger, Becker Underwood, Inc., 5 pages, Feb. 25, 2009.
Material Safety Data Sheet for Harmonizer, Petro-Canada Lubricants Inc., 6 pages, May 6, 2011.
Material Safety Data Sheet for JMS Stylet-Oil, 4 pages, Mar. 1, 1994.
Material Safety Data Sheet for Kannar Turfkare Green, 1 page, Sep. 18, 2007.
Material Safety Data Sheet for Killex Lawn Weed Control Concentate (Ortho), Scotts Canada Ltd., 7 pages, Sep. 13, 2005.

(56) References Cited

OTHER PUBLICATIONS

Material Safety Data Sheet for Lambent MFF 159-100, Lambent Technologies Corp., 3 pages, Apr. 4, 2006.
Material Safety Data Sheet for Lambent MFF-199 SW, Lambent Technologies Corp., 3 pages, Jan. 31, 2005.
Material Safety Data Sheet for PEPTOIL, Drexel Chemical Company, 1 page, Jan. 7, 2005.
Material Safety Data Sheet for Regreen™ Turfgrass Colorant, Precision Laboratories, Inc., 3 pages, Mar. 1, 2010.
Material Safety Data Sheet for Rovral Green GT Flowable Fungicide, Bayer CropScience Inc., 9 pages, Mar. 2, 2011.
Material Safety Data Sheet for Silsurf A008-UP, Siltech Corporation, 4 pages, Aug. 21, 2009.
Material Safety Data Sheet for SUNSPRAY 6E, Jun. 1, 2009, [retrieved on Sep. 30, 2014]. Retrieved from the Internet: <URL: http://www.recarroll.com/cw3/Assets/product files/Sunspray 6E.pdf>, 5 pages.
Material Safety Data Sheet for SURF AC 820, Drexel Chemical Company, 1 page, Jul. 22, 2005.
Material Safety Data Sheet for Sylgard 309 Silicone Surfactant, Dow Corning Corporation, 9 pages, Apr. 5, 2001.
McCarty and Whitwell, "Plant Growth Regulators for Fine Turf," Clemson University, South Carolina, archived Sep. 15, 2009. Retrieved from the Internet: <URL: http://www.clemson.edu/extension/horticulture/turf/pest_guidelines/growth_regulators.html>, 1 page.
McCowan, "Turf Herbicide Rx: Add Oil," Agricultural Chemicals, 23(4):18-21, 1968.
McCullough et al., "Ethephon and Trinexapac-ethyl Influence Creeping Bentgrass Growth, Quality, and Putting Green Performance," Plant Management Network, 2006. Retrieved from the Internet: <URL: http://www.plantmanagementnetwork.org/publats/research/2006/creeping/>, 7 pages.
McCullough et al., "Plant Growth Regulator Regimens Reduce Poa annua Populations in Creeping Bentgrass," *Plant Management Network*, 6 pages, Mar. 4, 2005.
McCullough, "Turfgrass Growth Regulators for Professional Managers," Extension Agronomist—Weed Science, Georgia Turf, retrieved Aug. 25, 2011. Retrieved from the Internet: <URL: http://commodities.caes.uga.edu/turfgrass/georgiaturf/publicat/PCRP2011 /PGR.pdf>, 2 pages.
Meister, Jr., Farm Chemicals, 141(1), pp. 4, 38, 42, 44, 46, 48, 77, 78, 80, 82, 84, 86, 92, 94, 96, Jan. 1978.
Mercier, "Use of the growth regulator paclobutrazol in the management of dollar spot of creeping bentgrass in Minnesota," *Phytoprotection*, 80(2):65-70, 1999.
Mergos et al., "Dielectric properties of nanopowder emulsions in paraffin oil," 2011 IEEE International Conference on Dielectric Liquids, Sep. 8, 2011.
Morris, "A Guide to NTEP Turfgrass Ratings," NTEP.org [online], 2011. Retrieved from the Internet: <URL: http://www.ntep.org/reports/ratings.htm>, 5 pages.
Mueller, "Fungicides: QoI Fungicides" Iowa State University, Available from: <URL: http://www.ipm.iastate.edu/ipm/icm/2006/5-22/fungicides.html>, 2 pages.
Mueller, "Fungicides: Triazoles," Intigrated Crop Management, Iowa State University, May 30, 2006. Retrieved from the Internet: <URL: http://www.ipm.iastate.edu/ipm/icm/2006/5-30/fungicides.htm >, 3 pages.
Murphy et al., "Plant Growth Regulators Used in Turfgrass Management," Georgia Turf, Retrieved on Aug. 25, 2011. Retrieved from the Internet: <http://commodities.caes.uga.edu/turfgrass/georgiaturf/WeedMngt/weedcontrol/PGR.htm>, 10 pages.
Murphy, "Turfgrass Growth Regulators for Professional Managers," Extension Agronomist—Weed Science, Georgia Turf, retrieved Aug. 25, 2011. Retrieved from the Internet: <URL: http://commodities.caes.uga.edu/turfgrass/georgiaturf/Publicat/PCRP2009/PGR.09.pdf>, 1 page.

Nalewaja et al., "Crop origin oils with grass control herbicides." *Proc. North Cent. Weed Control Conf.*, vol. 38, p. 3, 1983 (Abstract).
Nelson and Shearer, "2, 4-D and Mycoleptodiscus terrestris for control of Eurasian watermilfoil," *Journal of Aquatic Plant Management*, 43: 29-34, 2005.
Notice for Mecoprop-P TGAC, Commonwealth of Australia Gazette No. NRA 3, 2 pages, Mar. 6, 2001.
Oregon State University, National Forage & Grasslands Cirriculumn, "Discuss the basics of grass growth," forages.oregonstate.edu [online] <URL: http://forages.oregonstate.edu/nfgc/eo/onlineforagecurriculum/instructormaterials/availabletopics/management/growth> copyright 2008, 6 pages.
Ostmeyer, "The Color Green," *Golf Course Management*, pp. 40, 44, Aug. 1994.
Palla et al., "Correlation of dispersion stability with surfactant concentration and abrasive particle size for chemical mechanical polishing (cmp) slurries," *Journal of dispersion science and technology*, 21(5):491-509, 2000.
Pamphlet for Daconil 2787 Flowable Fungicide, Syngenta Crop Protection Canada, Inc., 9 pages, May 2004.
Pamphlet for Daconil Ultrex Fungicide, Syngenta Crop Protection Canada, Inc., 9 pages, May 2004.
Patton and Latin, "Turfgrass Disease Profiles: Rhizoctonia Large Patch," Purdue University, Retrieved from the Internet: <URL: https://www.extension.purdue.edu/extmedia/BP/BP-117-W.pdf> Feb. 2005, 3 pages.
Pavlista, "Paraffin enhances yield and quality of the potato cultivar Atlantic," *J. Prod. Agric.*, 8(1):40-42, 1995.
Perry, "Ground Covers: Specifications and Costs," *California Turfgrass Culture*, 21(3):21-22, 1971.
Perry, "Silicone Surface-Active Agents," Dow Corning Corporation, 2005. Retrieved from the Internet: <URL: http://www.dowcorning.com/content/publishedlit/26/1365.pdf>, 12 pages.
Pest Control for Professional Turfgrass Managers 2011, North Carolina State University, retrieved on Sep. 15, 2011. Retrieved from the Internet: <URL: http://www.turffiles.ncsu.edu/PDFFiles/004176/AG408PestControl_Prof- essionals.pdf>, 58 pages.
Pesticide Product Label System (PPLS), Search Results for PureSpray Oil 10E, Approval dates Apr. 21, 2000, Jul. 23, 2002, Sep. 24, 2003, Mar. 5, 2004. EPA Office of Pesticide Programs. Retrieved from the Internet: <http://oaspub.epa.gov/pestlabl/ppls.srchreslt?CompNum=69526&ProdNum=5>, 26 pages.
Platte Chemical Co., "Product Information Bulletin: Salvo: A premium broadleaf herbicide for use in corn, small grains, grass pastures, reangeland and other crop and noncrop areas," 6 pages, 2001.
Product Bulletin for Caltex, Caltex Australia, retrieved Aug. 2, 2006. Retrieved from the Internet: <URL: http://www.caltex.com.au/products_oil_detail_print.asp?id=229>, 2 pages.
Product Information—Sunoco Sunspray 11N/11E, 1 page, 2009.
Product Information Sheet for Sylgard 309 Silicone Surfactant, Dow Corning Corporation, 4 pages, May 2004.
Propiconazole Pesticide Information Profile, Extension Toxicology Network, Oct. 1997. Retrieved from the Internet: <URL: http://pmep.cce.cornell.edu/profiles/extoxnet/metiram-propoxur/propiconazole-ext.html>, 6 pages.
PureSpray Spray Oil 10E, Delaware Department of Agriculture Pesticide Database Searches, 2 pages, retrieved Apr. 7, 2005.
Puterka "Fungal pathogens for arthropod pest control in orchard systems: mycoinsecticidal approach for pear psylla control," *BioControl*, 44(2):183-209, 1999.
Quantification of Phosphorus in Water Based Green Pigments, 1 page, 2009.
Quicksheet for SALVO Herbicide, UAP Canada, 4 pages, 2006.
Rieke, "Thatchremoval," *California Turfgrass Culture*, 21(3):19-20, 1971.
Ross et al., "The Effect of the Plant Growth Regulator Primo on Winter Hardiness Levels," Prairie Turfgrass Research Centre, retrieved on Aug. 25, 2011. Retrieved from the Internet: <URL: http://www.oldscollege.ca/ptrc/2004_ar/Primohardiness02-05.htm>, 4 pages.

(56) References Cited

OTHER PUBLICATIONS

Samoucha et al., "Synergism in fungicide mixtures against Pseudoperonospora cubensis," *Phytoparasitica*, 16(4):337-342, 1988.
Sarkissian IV et al., "Regulation of mitochondrial activity by indoleacetic acid," *Biochim Biophys Acta.*, 128(3):413-418, Dec. 14, 1966.
Schott et al., "Effects of adjuvants on herbicidal action. III. Effects of petroleum and rapeseed oils on diclofop-methyl action on ryegrass," *Agronomie*, 11(1):27-34, 1991.
Schutte et al., "Application of Azoxystrobin for Control of Benomyl-Resistant Guignardia citricarpa on 'Valencia' Oranges in South Africa," *Plant Dis.*, 87(7): 784-788, Jul. 2003.
Scotts Canada Home: Killex Concentrate, Retrieved Aug. 2, 2006. Retrieved from the Internet: <URL: http://scottscanada.calindex.cfmlevent1ProductGuide.product/ documentld/30B255B82B>, 2 pages.
Shaposhnikov et al., "Carboxy-substituted phthalocyanine metal complexes," *Russian journal of general chemistry*, 75(9): 1480-1488, 2005.
Shearman et al., "Colorant effects on dormant buffalograss turf performance," *HortTechnology*, 15(2), 244-246, 2005.
Short and Castner, "Turfgrass Insects Sheet 1," University of Florida, Nov. 1992, reviewed Jun. 2005. Retrieved from the Internet: <URL: http://edis.ifas.ufl.edu/in025>, 2 pages.
Short and Castner, "Turfgrass Insects Sheet 2," University of Florida, Nov. 1992, reviewed May 2003. Retrieved from the Internet: <URL: http://edis.ifas.ufl.edu/in026>, 2 pages.
Smitley and Davis, "Black Cutworms," Michigan State University Turfgrass Science, archived on Feb. 12, 2010. Retrieved from the Internet: <URL: http://www.turf.msu.edu/black-cutworms>, 2 pages.
Soomary et al., "Evaluation of Fungicides for Control of the Leaf Spot Disease Caused by Mycosphaerella eumusae on Banana in Mauritius," Food and Agricultural Research Council, Proceedings Fourth Annual Meeting of Agricultural Scientists, pp. 61-65, Feb. 2001.
Specimen Label for AGRI-DEX, Helena Chemical Company, 2 pages, 2005.
Specimen Label for Banner MAXX, Syngenta Crop Protection, Inc., 31 pages, May 2004.
Specimen Label for BLENDEX VHC, Helena Chemical Company, 2 pages, May 2006.
Specimen Label for Chipco Signature, Bayer CropScience Pty Ltd, 2 pages, May 2004.
Specimen Label for Civitas, Petro-Canada Lubricants, Inc., 9 pages, May 2004.
Specimen Label for Cleary 3336 Plus, Cleary Chemical Corporation, 4 pages, May 2004.
Specimen Label for Fore 80WP Rainshield, Dow AgroSciences, 7 pages. Revised Jan. 8, 2007.
Specimen Label for Grass Greenzit: Permanent Green Pigment for Grass, 2 pages, 1998.
Specimen Label for Harmonizer, Petro-Canada Lubricants, Inc., 1 page, May 2004.
Specimen Label for Killex, Scotts, Canada Ltd., 6 pages, Jul. 23, 2001.
Specimen Label for Peptoil, Drexel Chemical Company, 2 pages, May 2004.
Specimen Label for Regreen, Precision Laboratories, Inc. 2 pages, Dec. 10, 2007.
Specimen Label for Rovral Green GT, Bayer CropScienc Inc., 2 pages, Mar. 19, 2009.
Specimen Label for Sil-Fact, Drexel Chemical Company, 1 page, May 2004.
Specimen Label for Sil-MES 100, Drexel Chemical Company, 1 page, May 2004.
Specimen Label for Surf-Ac 820, Drexel Chemical Company, 1 page, May 2004.
Specimen Label for Trimec Classic, PBI/Gordon Corporation, 2 pages, 1973.
Specimen Label for Trimec Southern, PBt/Gordon Corporation, 2 pages, 1987.
STN Database accession No. 1939:39478, 1 page, Dec. 16, 2001.
Technical Data Sheet for Lambent MFF 159-100, Lambent Technologies Corp., 1 page, May 2004.
Technical Data Sheet for Lambent MFF-199 SW, Lambent Technologies Corp., 1 page, May 2004.
Technical Data Sheet for Silsurf A008-UP, Siltech Corporation, 1 page, May 2004.
Technical Information for Lutensol AT types, BASF SE, 10 pages, May 2004.
Technical Sheet for Green Lawnger, Becker Underwood, Inc. 1 page, Nov. 2010.
Templeman, "The effect of some plant growth-substances on dry-matter production in plants," Empire J Exp Agric., 7(1):76-88, Jan. 1, 1939.
The Seed Site, "Monocots and Dicots," captured Feb. 24, 2010. Retrieved from the Internet: <URL: http://web.archive.org/web/20100224074428/http://theseedsite.co.uk/monocot.html >, 2 pages.
Trathnigg et al., "Molecular characterization of ethoxylates by complementary chromatographic techniques. Evaluation of efficiency and reliability," *Tenside Surf. Det.*, 40(3), 148-154, 2003.
Tu et al., "Weed control methods handbook: tools and techniques for use in natural areas," *The Nature Conservancy*, Wildland Invasive Species TEAM, version Apr. 2001, 219 pages.
Turfgrass Pest Control, West Virginia University, retrieved on Aug. 22, 2011. Retrieved from the Internet: <URL: http://www.wvu.edu/.about.exten/infores/pubs/pest/pcerti19.pdf>, 12 pages.
University of Arkansas, "Turf Tip—MSMA, Fungicide synergism, Buffalograss, Pythium." Retrieved from the Internet: <URL: http://turf.uark.edu/turfhelp/archives/030509.html> Mar. 5, 2009, 3 pages.
Unruh and Brecke, "Plant Growth Retardants for Fine Turf and Roadsides/Utilities," University of Florida, Apr. 1999, reviewed Sep. 2006, retrieved on Aug. 24, 2011. Retrieved from the Internet: <URL: http://edis.ifas.ufl.edu/pdffiles/WG/WG06400.pdf>, 5 pages.
Vallad and Goodman et al., "Systemic Acquired Resistance and Induced Systemic Resistance in Conventional Agriculture," *Crop Science*, 44(6):1920-1934, 2004.
Van Dam and Kurtz, "A Turfgrass Colorant Study," California Turfgrass Culture, 21(3):17-19, Summer 1971.
van Haeringen et al., "The Development of Solid Spectral Filters for the Regulation of Plant Growth," *Photochemistry and Photobiology*, 67(4):407-413, Apr. 1998.
VanBibber, "Putting the Numbers to PGRs," Grounds Maintenance, 2008. Retrieved from the Internet: <URL: http://grounds-mag.com/chemicals/grounds_maintenance_putting_numbers_pgrs/>, 6 pages.
Vann et al., "Rhizoctonia Large Patch Disease of Zoysiagrass and Bermudagrass," University of Arkansas Division of Agriculture, <https://www.uaex.edu/publications/PDF/FSA-7527.pdf> Mar. 1, 2007, 2 pages.
Vincelli, "Chemical Control of Turfgrass Diseases 2011," University of Kentucky College of Agriculture, <URL: http://pest.ca.uky.edu/PSEP/Manuals/ppal.pdf>, 24 pages.
Vol'pin et al., "Redox and fungicidal properties of phthalocyanine metal complexes as related to active oxygen," *Journal of Inorganic Biochemistry*, 81(4): 285-292, 2000.
Walsh et al., "Biology and management of dollar spot (*Sclerotinia homoeocarpa*); an important disease of turfgrass," *HortScience.*, 34(1): 13-21, 1999.
Wang, "Pesticide Pharmaceutics," *China Agriculture Press*, pp. 142-143, Aug. 2009, [English translation], 5 pages.
Wicks, "Control of grapevine powdery mildew with mineral oil: an assessment of oil concentration and spray volume," *Australian Journal of Grape and Wine Research*, 5: 61-65, 1999.
Wikipedia, "2,4-Dichlorophenoxyacetic acid," retrieved on Aug. 29, 2006. Retrieved from the Internet: <URL: http://en.wikipedia.orglwikii2%2C4-D>, 3 pages.

(56) References Cited

OTHER PUBLICATIONS

Womack et al., "A vegetable oil-based invert emulsion for mycoherbicide delivery," *Biological Control*, 6(1), 23-28, 1996.
Yang et al., "Infection of leafy spurge by Alternaria alternata and A. angustiovoidea in the absence of dew," *Phytopathology*, 83(9): 953-958, 1993.
Youngner et al., "Colorants for Dormant Bermuda and Other Subtropical Grasses," *Southern California Turfgrass Culture*, 8(1):7-8, 1958.
Youngner, "Gibberellic acid on Zoysia grasses," *Southern California Turfgrass Culture*, 8:5-6, 1958.
Youngner, "Kikuyugrass, Pennisetum Clandestinum, and Its Control," *Southern California Turfgrass Culture*, 8(1):1-4, Jan. 1958.
Zhengdong, "Application of SK EnSpray Oil," Pesticide Science and Administration, 28(10):25-29, Dec. 31, 2007.
European Communication Pursuant to Article 94(3) EPC for European Application No. 12793,919.7, dated Feb. 14, 2017, 5 pages.
International Preliminary Report on Patentability for PCT International Application No. PCT/CA2007/001762, dated Apr. 7, 2009, 7 pages.
International Preliminary Report on Patentability for PCT International Application No. PCT/CA2009/000862, dated Jan. 5, 2011, 7 pages.
International Search Report for PCT International Application No. PCT/CA2007/001762, dated Jan. 24, 2008, 2 pages.
International Search Report for PCT International Application No. PCT/CA2009/000862, dated Sep. 30, 2009, 5 pages.
Written Opinion for PCT International Application No. PCT/CA2007/001762, dated Jan. 24, 2008, 6 pages.
Written Opinion for PCT International Application No. PCT/CA2009/000862, dated Sep. 30, 2009, 6 pages.

* cited by examiner

Fig. 11  Typhula ishikariensis plots

Fig. 12 Typhula incarnata plots

TURFGRASS FUNGICIDE FORMULATION WITH PIGMENT

CROSS-REFERENCE TO RELATED APPLICATIONS

This application claims the benefit of U.S. Provisional Patent application Ser. No. 61/075,821, filed Jun. 26, 2008 and U.S. Provisional Patent application Ser. No. 61/147,523, filed Jan. 27, 2009, the entirety of which are incorporated herein by reference.

FIELD OF THE INVENTION

Embodiments of the invention relate to oil-in water emulsions having fungicidal properties when applied to turfgrass and more particularly, to oil-in-water emulsions having stable dispersions of pigment therein for enhancing fungicidal activity and for imparting color to the turfgrass when applied thereon.

BACKGROUND OF THE INVENTION

In Applicant's previous applications, such as in co-pending US-2005-0261379-A1, the entirety of which is incorporated herein by reference, the Applicant has previously described the use of an oil-in-water emulsion as means of controlling turf diseases. A disadvantage may be that certain grasses such as varieties of bentgrass are sensitive to oil-in-water formulations which can often have the undesired effect of discolouring the grass especially under the heat of summer. Although the health of the plant is not negatively affected, the discolouration can be problematic from an aesthetic perspective.

Pigment colorants, such as phthalocyanine compounds, are known to have been used in the turf industry, both in the presence and the absence of fungicide. The known literature teaches the use of pigment color, such as non-chlorinated copper phthalocyanine as a means of colouring the grass or turf. One such example is US 2006/0293188 A1 to Norton (Bayer Cropscience LP), the entirety of which is incorporated herein by reference. Additional references include U.S. Pat. No. 5,336,661 to Lucas, U.S. Pat. No. 5,643,852 to Lucas and U.S. Pat. No. 5,599,804 to Mudge, the entirety of which are incorporated herein by reference.

Others references of interest include German application DE 2511077 published in 1978, which teaches cobalt phthalocyanine as a colourant in the absence of an acid. In an English abstract for JP 03-221576 to Nippon Chemical Works, published Sep. 30, 1991, the disclosed formulation uses phthalocyanine "green", an anionic dispersant, and acrylic acid ester-styrene and water.

Unfortunately, none of the teachings provide a solution for use of pigment in oil-in-water emulsion systems as Applicant has found that pigments, such as polychlorinated copper phthalocyanine, appear to clump or coagulate and thereafter quickly fall out of suspension rendering the formulation unworkable.

Clearly, there is a need to provide an oil-in-water fungicidal formulation which contains a dispersion of pigment or colorant therein in which the colorant remains stably dispersed for application to turfgrass.

SUMMARY OF THE INVENTION

Applicant has discovered that one can generate stable compositions of pigment in a high oil-in-water emulsion environment by the addition of a small amount of a silicone surfactant of a specific chemistry in combination with a small amount of an emulsifier of specific chemistry. The silicone surfactant and emulsifier are thought to act as dispersants for the pigment within the oil-based formulation, prior to dilution for forming the oil-in-water emulsion and in the final oil-in-water emulsion. Formulations according to embodiments of the invention have an enhanced efficacy in treating turfgrass disease.

In addition, Applicant has found that the incorporation of a pigment dispersed into the oil-in-water emulsion disclosed herein has a synergistic impact and improves the overall efficacy of disease control of the active fungicidal components. At the same time, the amount of oil required to achieve adequate disease control can be reduced to about half the amount of oil compared to the amount required if the oil is used alone, thus further reducing the possibility of phytotoxicity. Further, discolouration issues which may occur on certain grasses, such as varieties of bentgrass that are sensitive to oil-in-water formulations especially under the heat of summer, are overcome by formulations prepared according to embodiments of the invention.

In addition, Applicant has determined that embodiments of the present invention have an unexpected synergistic effect when mixed with conventional chemical fungicides such as demethylation inhibitors (such as propiconazole), methyl benzimidazole carbamate (such as thiophanate-methyl) and dicarboximide (such as iprodione). When mixed with formulations according to embodiments of the invention, the dosage of such conventional chemical fungicides can be reduced significantly, such as to about 50% the recommended label rates, as well permitting significant reduction in the required dosage of the formulations of the present invention.

Advantageously, the present invention also acts to suppress certain turf insects such as fall armyworms and sod webworms.

In a broad aspect of the invention, a fungicidal formulation for application to turfgrass comprises: an oil-in water emulsion comprising a paraffinic oil, a suitable emulsifier and water; polychlorinated (Cu II) phthalocyanine; and a silicone surfactant selected from the group consisting of trisiloxanes and silicone polyethers of Formula I

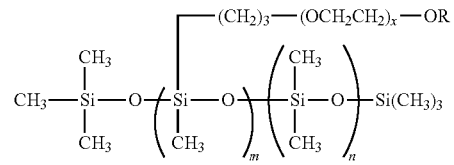

(Formula I)

where: R=H, $CH_3$ or $COCH_3$; x=1 to 24; n=0 or ≥1; m=1, wherein the polychlorinated (Cu II) phthalocyanine is maintained in dispersion in the oil-in-water emulsion for delivery to turfgrass.

In another broad aspect, a method for preparing the fungicidal formulation comprises: preparing a first composition having the paraffinic oil; and the suitable emulsifier selected from the group consisting of natural and synthetic alcohol ethoxylates, including polyoxyethylene (4 to 12) lauryl ether ($C_{12}$), polyoxyethylene (10) cetyl ether ($C_{16}$), polyoxyethylene (10) stearyl ether ($C_{18}$), polyoxyethylene (10) oleyl ether ($C_{18}$ monounsaturated), polyoxyethylene (2 to 11) $C_{12}$-$C_{15}$ alcohols, polyoxyethylene (3 to 9) $C_{11}$-$C_{14}$ alcohols, polyoxyethylene (9) $C_{12}$-$C_{14}$ alcohols; polyoxyethylene (11) $C_{16}$-$C_{18}$ alcohols, and polyoxyethylene (20) $C_{12}$-$C_{15}$ alcohols; alcohol alkoxylates including butyl polyoxyethylene/polyoxypropylene block copolymer; alkyl polysaccharides including $C_8$-$C_{11}$ alkylpolysaccharides; glycerol oleate; polyoxyethylene-polyoxypropylene block copolymers of MW 1100 to 11400 and 10 to 80% EO; nonyl phenol ethoxylates including polyoxyethylene (2 to 8) nonylphenol; polymeric surfactants including graft copolymer such as polymethacrylic acid and acrylate with polyoxyethylene chains and random copolymer with ester and ether group; polyethylene glycols including MW: 200 to 8000, MW: 400 PEG dioleate, and MW: 600 PEG dioleate; sorbitan fatty acid ester ethoxylates including polyoxyethylene (20) sorbitan tristearate, polyoxyethylene (20) sorbitan monooleate, polyoxyethylene (5) sorbitan monooleate, and polyoxyethylene (20) sorbitan trioleate; and mixtures thereof; preparing a second composition being and aqueous dispersion of the polychlorinated (Cu II) phthalocyanine; adding the silicone surfactant to one or both of the first and second compositions; and thereafter prior to use; and mixing an effective amount of the first composition with an effective amount of the second composition, the polychlorinated (Cu II) phthalocyanine being dispersed and stable therein.

In another broad aspect, a method for preparing the fungicidal formulation comprises: preparing a single composition having the paraffinic oil; the suitable emulsifier selected from the group consisting of natural or synthetic alcohol ethoxylates including polyoxyethylene (4 to 7) lauryl ether ($C_{12}$); polyoxyethylene (10) cetyl ether ($C_{16}$); polyoxyethylene (2 to 11) $C_{12}$-$C_{15}$ alcohols; polyoxyethylene (3 to 9) $C_{11}$-$C_{14}$ alcohols; polyoxyethylene (9) $C_{12}$-$C_{14}$ alcohols; polymeric surfactants including graft copolymer such as polymethacrylic acid and acrylate with polyoxyethylene chains; and random copolymer with ester and ether group; sorbitan fatty acid esters including sorbitan tristearate; and sorbitan trioleate; and mixtures thereof; the polychlorinated (Cu II) phthalocyanine being dispersed in oil; and the silicone surfactant, wherein the silicone surfactant further comprises polyethylene glycols (PEG) according to Formula (IV):

$$R_1\text{—}O\text{—}(CH_2\text{—}CH_2\text{—}O)_n\text{—}R_2 \quad \text{Formula (IV)}$$

where: $R_1$=H or $CH_2$=CH—$CH_2$ or $COCH_3$.

DETAILED DESCRIPTION OF THE PREFERRED EMBODIMENT

Prior Art

Figure 1:
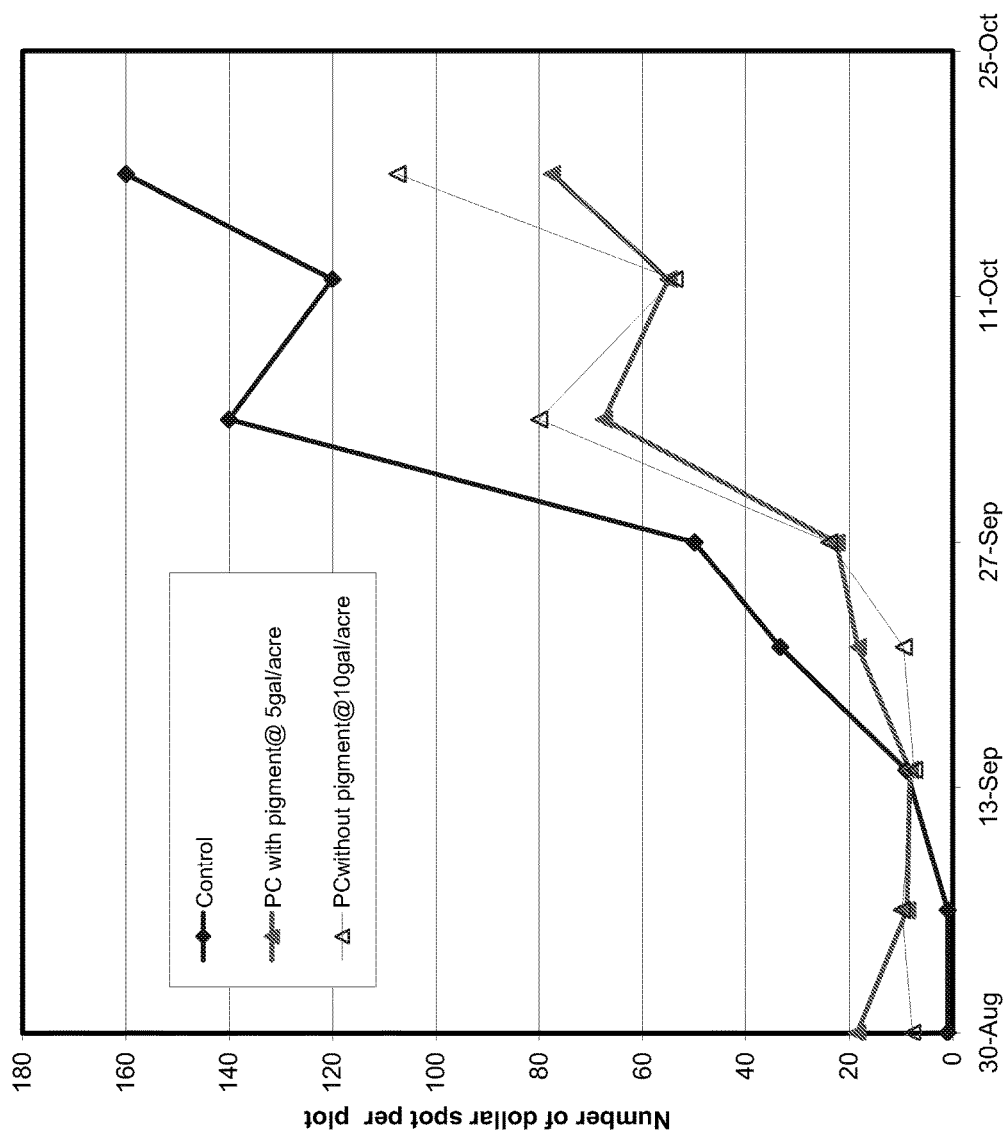
FIG. 1 is a graphical representation of the results of Example 7 showing a synergistic effect resulting from the addition of pigment to an oil-in-water fungicidal formulation prepared as a 2-pack formulation, permitting use of the formulation at rates lower than predicted rates when treating turfgrass infected with dollar spot disease.

Applicant has found that the addition of colorants or pigments, based upon the teachings in the prior art, to oil-in-water emulsion formulations resulted in unstable dispersions of the pigment therein.

In the following Examples 1 through 3, polychlorinated Cu(II) phthalocyanine pigment (available from Sun Chemical as SUNSPERSE® Green 7, ~60% polychlorinated Cu (II) phthalocyanine dispersed in water or as Pigment Green 7 powder available from Hercules Exports, Mumbai, India) was added to a synthetic isoparaffinic oil (N65DW available from Petro-Canada, Calgary, AB, Canada), with or without polyoxyethyene lauryl ether, $C_{10}$ to $C_{16}$ alcohol ethoxylates, and glycerol oleate as an emulsifier (available as PC Emuls Green, from Petro-Canada, Calgary, AB, Canada) and was diluted in water to form the oil-in-water emulsion suitable for application to turfgrass.

In each of Examples 1-3, the pigment coagulated or formed clumps which rapidly separated out and/or resulted in phase separation of the formulations. Thus, the pigment did not remain dispersed in the formulations and therefore the formulations were not usable to reliably and evenly impart color to turfgrass.

Example 1 a. 0.3 to 0.5 wt % polychlorinated Cu (II) phthalocyanine (SUNSPERSE® Green 7)
b. 10 wt % synthetic isoparaffinic oil (N65DW)
c. 89.5 wt % water

Example 2 a. 0.3-0.5 wt % polychlorinated CU (II) phthalocyanine (SUNSPERSE® Green 7)
b. 10 wt % isoparaffinic oil (N65DW)
c. 0.1 wt % emulsifier (PC Emuls Green)
d. 89.4 wt % water

Example 3 a. 0.5 wt % polychlorinated Cu (II) phthalocyanine (Pigment Green 7 powder)
b. 10 wt % isoparaffinic oil (N65DW)
c. 0.1 wt % emulsifier (PC Emuls Green)
d. 89.4 wt % water

Embodiments of the Invention

As shown in Example 4, Applicant has found that the incorporation of specific silicone surfactants and emulsifier dispersants added to an oil-in-water emulsion, having a significant portion of oil therein and containing pigment, results in the pigment being stably dispersed therein for application, such as by spraying, to turfgrass.

The non-aqueous portion of the oil-in-water portion is typically applied at rates from about 1 gal/acre (0.093 L/100 m$^2$) to about 15 gal/acre (1.395 L/100 m$^2$). The total spray volume of the oil-in-water emulsion is typically from about 20 gal/acre (1.9 L/100 m$^2$) to about 200 gal/acre (18.6 L/100 m$^2$).

Example 4

A formulation according to an embodiment of the invention was prepared as follows:
a. 0.5 wt % polychlorinated Cu (II) phthalocyanine (SUNSPERSE® Green 7)
b. 10 wt % isoparaffinic oil (N65DW)
c. 0.1 wt % emulsifier (PC Emuls Green)
d. 89.3 wt % water
e. 0.1 wt % silicone surfactant (Lambent MFF-199 SW)

An exemplary silicone super-wetting agent, such as Lambent MFF-199 SW (available from Lambent Technologies, a division of Petroferm, Inc., Gurnee, Ill., USA. MFF-199-SW) is a silicone copolyol, containing a hydrogen end group and one pendant polyethylene oxide group and has an average molecular weight between 600 to 1000 Daltons.

Lambent MFF-199 is a totally different class of silicone oil compared to common linear or cyclic polydimethylsiloxane. Lambent MFF-199 is a trisiloxane with an ethoxylated alkyl group having a hydrogen end group (H-End). The number of ethoxylation group is in the range of 1-20.

The suggested structure is as follows:

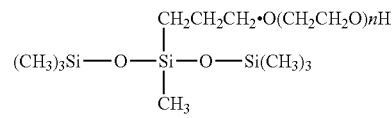

where: n=1-20 and average n=8

2-Pack Formulation

In an embodiment of the invention, a first composition (Pack A) is prepared containing the paraffinic oil and a suitable emulsifier. A second composition (Pack B) is prepared comprising a polychlorinated Cu (II) phthalocyanine. The polychlorinated Cu (II) phthalocyanine can be provided as a powder dispersed in water or as a ready to use aqueous dispersion.

A silicone surfactant, such as Lambent MFF 159-100 or MFF 199 SW or other suitable silicone surfactant as described below can be added entirely to Pack A or to Pack B. Alternatively, the silicone surfactant can be split between Pack A and Pack B.

Immediately prior to use, an effective amount of each of Pack A and Pack B are mixed together to form the fungicidal dispersion which is further diluted in water to the desired concentration, as described below, for delivery to turfgrass at a predetermined dosage rate.

More particularly, in embodiments of the invention, the effective amount of Pack A is mixed with some or all of the water which would be required to obtain a desired concentration so as to form an emulsion. Thereafter, the effective amount of Pack B and any remaining water are added to the emulsion and the mixture is delivered to turfgrass as an oil-in-water emulsion at a predetermined dosage rate.

The silicone and emulsifier are selected to provide an intermolecular hydrophilic and lipophilic balance upon mixing of Pack A and Pack B so as to substantially prevent the polychlorinated Cu (II) phthalocyanine from clumping and rapidly separating out of suspension in the presence of the oil phase during application to the turfgrass.

Suitable silicone surfactants comprise trisiloxanes or silicone polyethers having a suitable alkoxy group with hydrogen end groups (H-capped), methyl end groups (CH$_3$ capped) or acetyl end groups (COCH$_3$ capped) according to the following formula (I):

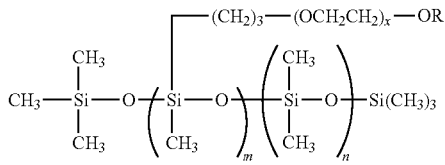

(Formula I)

Where:

| | | | | |
|---|---|---|---|---|
| R = H; | x = 1 to 24; | n = 0; | m = 1; | H- capped trisiloxane |
| R = H; | x = 1 to 24; | n ≥ 1; | m = 1; | H - capped silicone polyethers |
| R = CH$_3$; | x = 1 to 24; | n = 0; | m = 1; | CH$_3$ - capped trisiloxane |
| R = CH$_3$; | x = 1 to 24; | n ≥ 1; | m = 1; | CH$_3$ - capped silicone polyethers |
| R = COCH$_3$; | x = 1 to 24; | n = 0; | m = 1; | COCH$_3$ - capped trisiloxane |
| R = COCH$_3$; | x = 1 to 24; | n ≥ 1; | m = 1; | COCH$_3$ - capped silicone polyethers |

Commercial preparations of the silicone surfactants above may or may not contain small amounts of polyethylene glycols (PEG) or other low molecular weight polydimethyl siloxanes (PDMS).

In embodiments of the invention, silicone surfactant is added in a range of about 0.1 wt % to about 5 wt % in the non-aqueous portion of the oil-in-water emulsion.

In an embodiment of the invention, the silicone surfactant, added in an amount of about 2 wt % in the non-aqueous portion of the oil-in-water emulsion, is an H-capped dimethyl methyl(polyethylene oxide) silicone polymer having a molecular weight from 200-6000 as shown below in Formula (II):

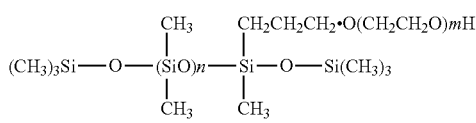

Formula (II)

where: n=2-70, the average n=44; m=2-16 and the average m=10.

Suitable emulsifiers are selected and added in amounts so as to generate a stable emulsion and to prevent phytotoxicity.

The emulsifier is added in a range from about 0.5 wt % to about 5 wt % in the non-aqueous portion of the oil-in-water emulsion. More particularly, in embodiments of the invention, the emulsifier is added in a range from about 1 wt % to about 3 wt % in the non-aqueous portion of the oil-in-water emulsion. In an embodiment of the invention, the emulsifier is added at about 2 wt % in non-aqueous portion of the oil-in-water emulsion.

The emulsifier is selected from the group consisting of:
Alcohol ethoxylates (natural and synthetic) including polyoxyethylene(4 to 12) lauryl ether (C12); polyoxyethylene (10) cetyl ether (C16); polyoxyethylene (10) stearyl ether (C18); polyoxyethylene (10) oleyl ether (C18 monounsaturated); polyoxyethylene (2 to 11) C12-C15 alcohols; polyoxyethylene (3 to 9) C11-014 alcohols; polyoxyethylene (9) C12-C14 alcohols; polyoxyethylene (11) C16-C18 alcohols; and polyoxyethylene (20) C12-C15 alcohols;
Alcohol alkoxylates including butyl polyoxyethylene/polyoxypropylene block copolymer;
Alkyl polysaccharides including C8-C11 alkylpolysaccharides;
Glycerol oleate;
Polyoxyethylene-polyoxypropylene block copolymers of MW 1100 to 11400 and 10 to 80% EO;
Nonyl phenol ethoxylates including polyoxyethylene (2 to 8) nonylphenol;
Polymeric surfactants including graft copolymer such as polymethacrylic acid and acrylate with polyoxyethylene chains and random copolymers with ester and ether groups;
Polyethylene glycols including MW: 200 to 8000; MW: 400 PEG dioleate; and MW: 600 PEG dioleate; and
Sorbitan fatty acid ester ethoxylates including polyoxyethylene (20) sorbitan tristearate; polyoxyethylene (20) sorbitan monooleate; polyoxyethylene (5) sorbitan monooleate; and polyoxyethylene (20) sorbitan trioleate.

Examples of 2-Pack Embodiment

In embodiments of the invention, a sufficient volume of Pack A was added to a volume of water required to obtain a desired concentration in the final formulation and was mixed to form an emulsion. Sufficient Pack B was added to the emulsion to result in a fungicidal dispersion which comprised:
an effective amount of paraffinic oil, being about 5 wt %;
about 0.1 wt % emulsifiers;
about 0.3 wt % polychlorinated Cu (II) phthalocyanine; and
about 0.1 wt % silicone surfactant.

The fungicidal dispersion was sprayed onto turfgrass at a rate of from about 50 gal/acre (4.7 L/100 m$^2$) to about 100 gal/acre (9.3 L/100 m$^2$).

Example 5

In an example of the 2-Pack embodiment of the invention, the following compositions (Pack A and Pack B) were prepared and mixed together as described to achieve the sprayable dispersion.

Pack A

| | Components | Chemical Description | Supplier Name | % by weight | Purpose in Formulation |
|---|---|---|---|---|---|
| 1 | N65DW | Highly saturated paraffinic oils with a carbon number distribution in the range of about C$_{16}$ to about C$_{35}$ | Petro-Canada | 96 | Active Ingredient |

-continued

| | Components | Chemical Description | Supplier Name | % by weight | Purpose in Formulation |
|---|---|---|---|---|---|
| 2 | PC Emuls Green | 1. Ethoxylated alcohols having primary C5-C20 carbon chains with an average of about 2 to about 7 ethoxylation groups 2. Glycerol Oleate | Petro-Canada | 2 | Emulsifier |
| 3 | Lambent MFF199 SW | Methyl (propylhydroxide, ethoxylated) bis (trimethylsiloxy) silane | Lambent Technologies Corp., Gurnee IL USA | 2 | Wetting agent/dispersant |

Pack B

| | Components | Chemical Description | Supplier Name | % by weight | Purpose in Formulation |
|---|---|---|---|---|---|
| 1 | SUNSPERSE ® Green 7 (GCD9957) | 58% polychlorinated Cu(II) phthalocyanine ($C_{32}HCl_{15}CuN_8$) dispersed in water | Sun Chemical Corp Performance Pigment Cincinnati OH USA | 100 | Colorant |

In the embodiment of the invention described in Example 5, all of the silicone surfactant was added to Pack A.

Example 6

In an example of the 2-Pack embodiment of the invention, the following components or compositions were prepared and mixed together as described to achieve the sprayable dispersion.

Pack A

| | Components | Chemical Description | Supplier Name | % by weight | Purpose in Formulation |
|---|---|---|---|---|---|
| 1 | N65DW | Highly saturated paraffinic oils with a carbon number distribution in the range of about $C_{16}$ to about $C_{35}$ | Petro-Canada | 98 | Active Ingredient |
| 2 | PC Emuls Green | 1. Ethoxylated alcohols having primary $C_5$-$C_{20}$ carbon chains with an average of about 2 to about 7 ethoxylation groups 2. Glycerol Oleate | Petro-Canada | 2 | Emulsifier |

Pack B

| | Components | Chemical Description | Supplier Name | % by weight | Purpose in Formulation |
|---|---|---|---|---|---|
| 1 | SUNSPERSE ® Green 7 (GCD9957) | 58% polychlorinated Cu(II) phthalocyanine ($C_{32}HCl_{15}CuN_8$) dispersed in water | Sun Chemical Corp Performance Pigment Cincinnati, OH USA | 83.8 | Colorant |
| 2 | Lambent MFF159-10 | Dimethyl, methyl (polyethylene oxide) silicone polymer | Lambent Technologies Corp., Gurnee IL USA | 16.2 | Wetting agent/dispersant |

In the embodiment of the invention described in Example 6, all of the silicone surfactant was added to Pack B.

Examples 7 to 10—2-Pack Formulation

Examples 7 to 10 were performed using a formulation prepared according to Example 5.

Example 7—Comparison of the Efficacy of the 2-Pack Formulation to a Formulation Without Pigment An embodiment of the invention was applied to creeping bentgrass (*Agrostis stolonifera*) at a close cut putting green height of 5 mm to determine the efficacy of an embodiment of the invention to control dollar spot. Dollar spot is caused by *Sclertinia Homeocarpa* and is the most common disease requiring control on golf courses throughout most of the world.

The embodiment of the invention, applied to the turfgrass at 5 gal/acre (0.5 L/100 m²) of the non-aqueous portion of the oil-in-water emulsion, was compared to the use a higher concentration of oil-in-water emulsion without pigment, applied at 10 gal/acre (1 L/100 m²) of the non-aqueous portion of the oil-in-water emulsion, and an inoculated control. The plots were inoculated with five strains of *Sclertinia Homeocarpa*, one week after initial chemical application.

The fungicides were applied in water at a total spray volume rate of about 129 gal/acre (12 L/100 m$^2$) using a wheel-mounted compressed air boom sprayer at 140 kPa. Applications were made at 14 day intervals. Weekly counts of dollar spot infection were conducted over the 6 week period.

Chemical Treatment List

| Treatment | Product per 100 m$^2$ | No. of Applications | Treatment Interval |
|---|---|---|---|
| Fungicide with pigment (2-pack) | 465 mL | 3 | 14 days |
| Fungicide without pigment | 930 mL | 3 | 14 days |

Conclusions

As shown in FIG. 1, acceptable control of dollar spot was achieved using the 2-pack fungicide at 5 gal/acre (0.5 L/100 m$^2$) with the addition of the polychlorinated Cu (II) phthalocyanine pigment dispersion, emulsifier and silicone additives.

The use of 5 gal/acre (0.5 L/100 m$^2$) of the non-aqueous portion of the 2-pack fungicide formulation performed substantially the same as using the oil-in-water emulsion alone at 10 gal/acre (1 L/100 m$^2$) of the non-aqueous portion. The data suggests a synergistic effect resulting from the addition of pigment, permitting use of the formulation at rates lower than predicted rates.

An additional benefit of the lower treatment rate is the reduced propensity for phytotoxicity which may be observed at high oil rates.

Example 8

A 2-Pack embodiment of the invention was applied to creeping bentgrass (*Agrostis stolonifera*) at a close cut putting green height of 5 mm to determine the efficacy of an embodiment of the invention to control dollar spot. Close cut turf is highly susceptible to dollar spot.

The 2-pack embodiment of the invention was compared to a chemical fungicide, DACONIL® 2787, also known as WEATHERSTIK™, available from Syngenta Crop Protection Canada, Inc. Guelph, Ontario, Canada, and an inoculated control. The trials were conducted on 8 year old PENNCROSS® creeping bentgrass (*Agrostis stolonifera*). The treatments were applied over a 7-week period and the turf and disease were monitored over a 9-week period to examine residual effects and grass recovery. A randomized complete block design having four replications was used and each treatment plot measure 1 m×2 m. The plots were inoculated with five strains of *Sclertinia Homeocarpa*, one day after initial chemical application.

Due to the close cutting of the turf in this example the disease pressure was extreme. The fungicides were applied in water at a total spray volume rate of 118 gal/acre (11 L/100 m$^2$) using a wheel-mounted compressed air boom sprayer at 140 kPa. Applications were made at 14 day intervals for both the DACONIL® and the 2-pack formulation. An additional plot was treated with applications of the 2-pack formulation at 7 day intervals. Weekly counts of dollar spot infection were conducted over the 7 week period.

Chemical Treatment List

| Treatment | Product per 100 m$^2$ | No. of Applications | Treatment Interval |
|---|---|---|---|
| DACONIL ® 2787 | 95 mL | 4 | 14 days |
| 2-pack fungicide | 465 mL | 4 | 14 days |
| 2-pack fungicide | 465 mL | 7 | 7 days |

Results

Figure 2:
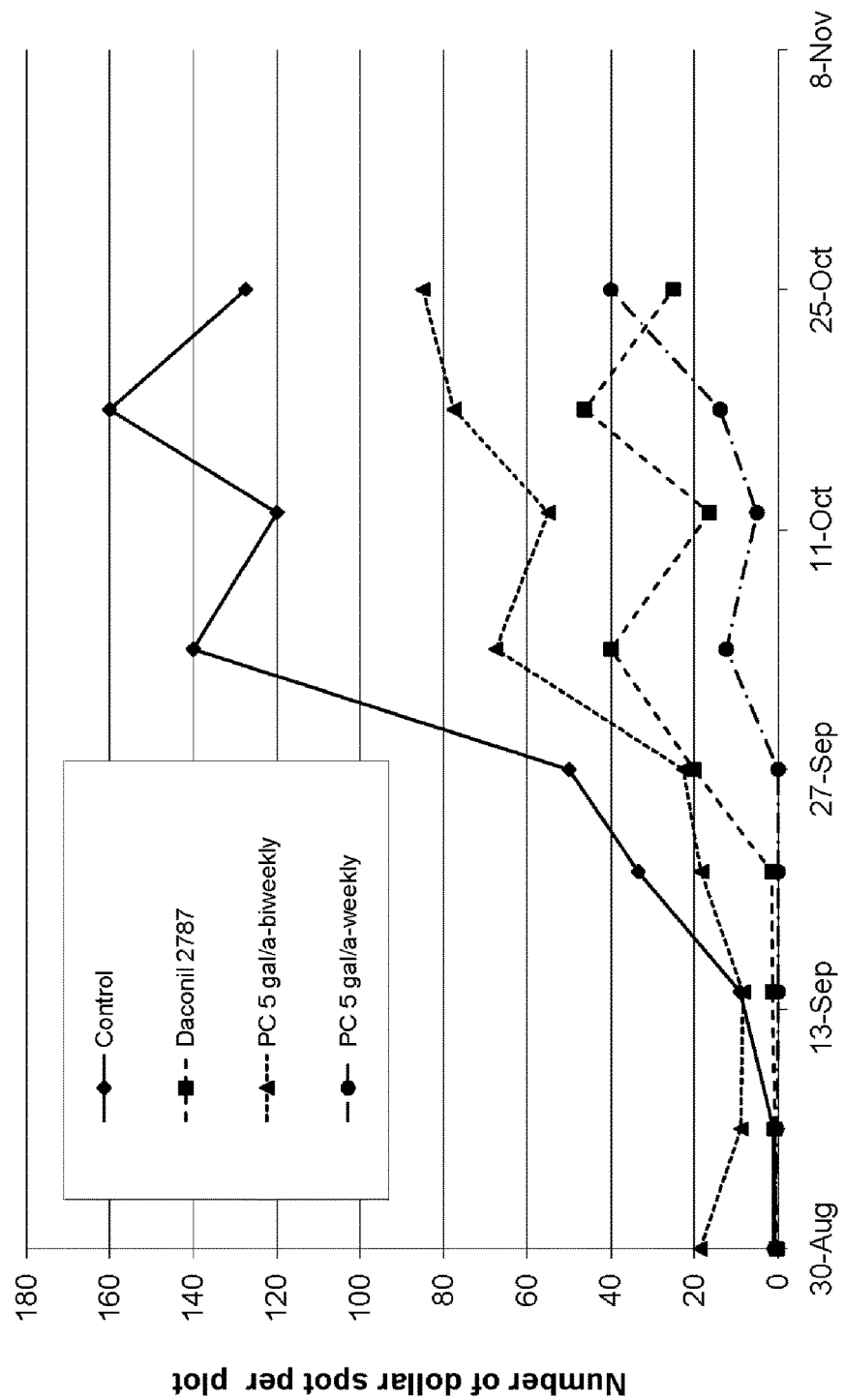
FIG. 2 is a graphical representation of the results of Example 8 showing the efficacy of the 2-pack fungicide applied at 5 gal/acre (non-aqueous portion) compared to conventional chemical fungicide, DACONIL® 2787, applied at the same rate for treating turfgrass infected with Dollar Spot disease.

As shown in FIG. 2, low levels of dollar spot disease were present on all of the plots at the start of the trial. Nearing the end of the trial, the disease levels in the control exceeded 100 spots per plot on the inoculated areas. All three chemical treatments showed significant suppression of dollar spot disease when compared to the control. The suppression of disease continued for about two weeks following the last application.

It was noted that when applied weekly, the 2-pack formulation performed substantially better than the 2-pack formulation or the DACONIL® applied at the recommended rate of biweekly. One of skill in the art would recognize therefore that, in cases of extreme dollar spot disease, efficacy of the 2-pack formulation is improved if applied more frequently.

Phytotoxicity was not observed in any of the treatments.

Conclusions

The 2-pack fungicide, applied at 5 gal/acre (0.5 L/100 m$^2$) of the non-aqueous portion performed substantially the same as the chemical fungicide, DACONIL® 2787.

In cases of extreme disease pressure the 2-pack formulation should be applied more frequently.

Example 9

An embodiment of the invention was applied to creeping bentgrass (*Agrostis stolonifera*) at a fairway height of 11 mm to determine the efficacy of an embodiment of the invention to control dollar spot. Dollar spot is caused by *Sclertinia Homeocarpa* and is the most common disease requiring control on golf courses throughout most of the world.

The embodiment of the invention was compared to a chemical fungicide, DACONIL® 2878, also known as WEATHERSTIK™, available from Syngenta Crop Protection Canada, Inc. Guelph, Ontario, Canada, and an inoculated control. The trials were conducted on 13 year old PENNCROSS® creeping bentgrass (*Agrostis stolonifera*). The treatments were applied over a 6-week period and the turf and disease were monitored to examine residual effects and grass recovery. A randomized complete block design having four replications was used and each treatment plot measure 1 m×2 m. The plots were inoculated with five strains of *Sclertinia Homeocarpa*, one week after initial chemical application.

The fungicides were applied in water at a total spray volume rate of 129 gal/acre (12 L/100 m$^2$) using a wheel-mounted compressed air boom sprayer at 140 kPa. Applications were made at 14 day intervals. Weekly counts of dollar spot infection were conducted over the 6 week period.

Chemical Treatment List

| Treatment | Product per 100 m$^2$ | No. of Applications | Treatment Interval |
|---|---|---|---|
| DACONIL ® 2787 | 95 mL | 3 | 14 days |
| 2-pack fungicide | 465 mL | 3 | 14 days |
| 2-pack fungicide | 930 mL | 3 | 14 days |

Results

Figure 3:
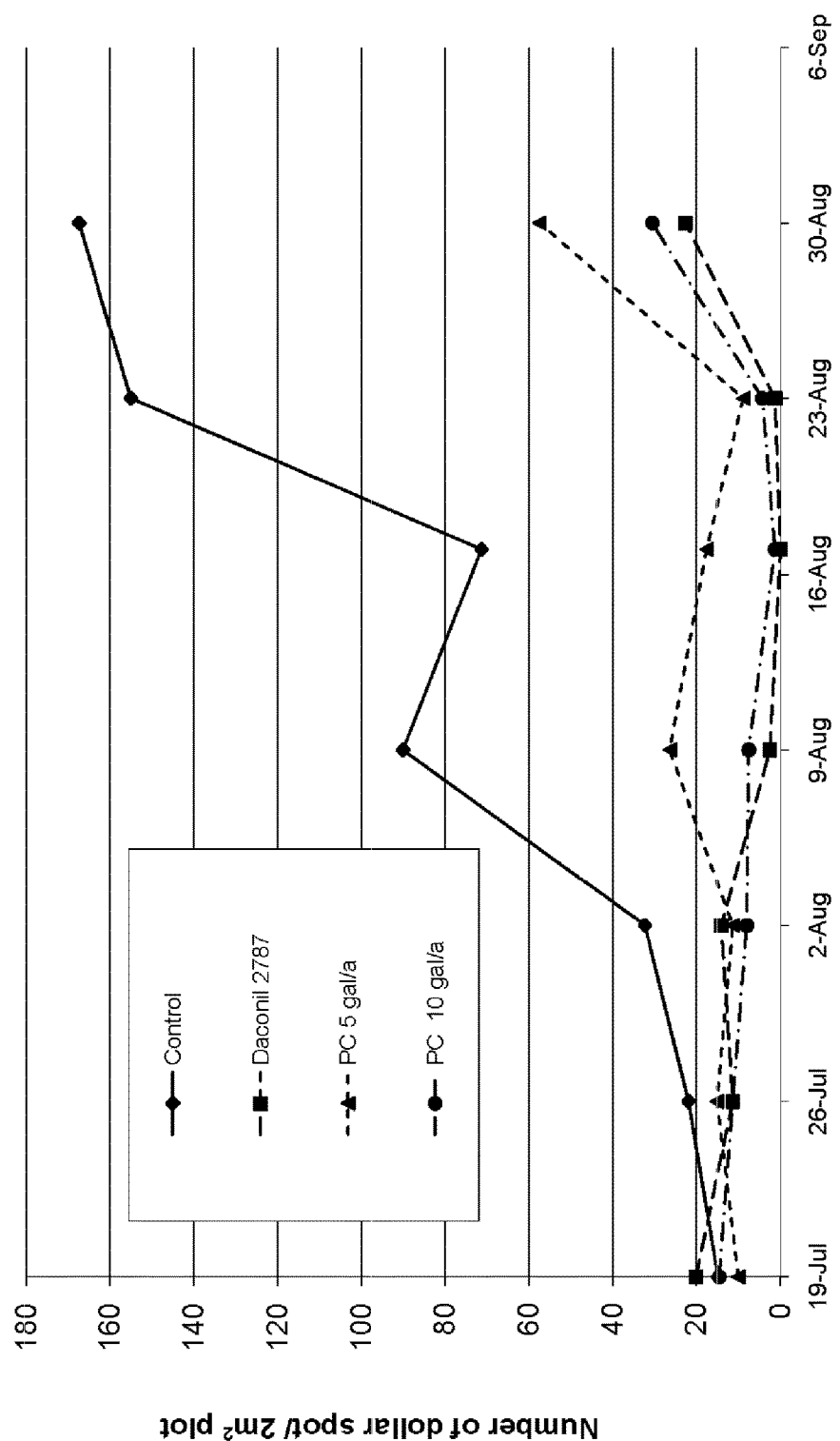
FIG. 3 is a graphical representation of the results of Example 9 showing the efficacy of the 2-pack fungicide, applied at both 5 gal/acre (non-aqueous portion) and 10 gal/acre (non-aqueous portion), compared to the chemical fungicide, DACONIL® 2787, for treating turfgrass infected with Dollar Spot disease.

As shown in FIG. 3, dollar spot disease was present on all of the plots at the start of the trial. All three treatments showed significant suppression of dollar spot disease when compared to the control. The suppression of disease continued for about two weeks following the last application.

Phytotoxicity was not observed in any of the treatments.

Conclusions

The 2-pack fungicide, applied at both 5 gal/acre (0.5 L/100 m$^2$) of the non-aqueous portion and 10 gal/acre (1 L/100 m$^2$) of the non-aqueous portion, performed substantially the same as the chemical fungicide, DACONIL® 2787.

Example 10

An embodiment of the 2-pack formulation was used to treat dollar Spot on *Poa Trivialis* (rough stalk bluegrass) overseeded Bermudagrass plot cut at putting green height. The 2-pack formulation was applied at 2.5 gal/acre (0.2 L/100 m$^2$) of the non-aqueous portion and was compared to a formulation prepared without the pigment, the silicone surfactant and the particular emulsifier and which was applied at 5 gal/acre (0.5 L/100 m$^2$) of the non-aqueous portion and to an untreated control.

The formulations were applied using a CO$_2$ backpack boom sprayer calibrated to deliver products in 2 gallons of water per 1000 sq ft (8 L/100 m$^2$) through two 8003 TEEJET® flat fan nozzles.

The turfgrass plots were divided into 4 blocks and treatments were assigned in a randomized complete block design. The plots were inoculated with 1 L of wheat seed infested with *Sclerotinia homoeocarpa*. Fungicide formulations were applied weekly for 8 weeks.

Figure 4:
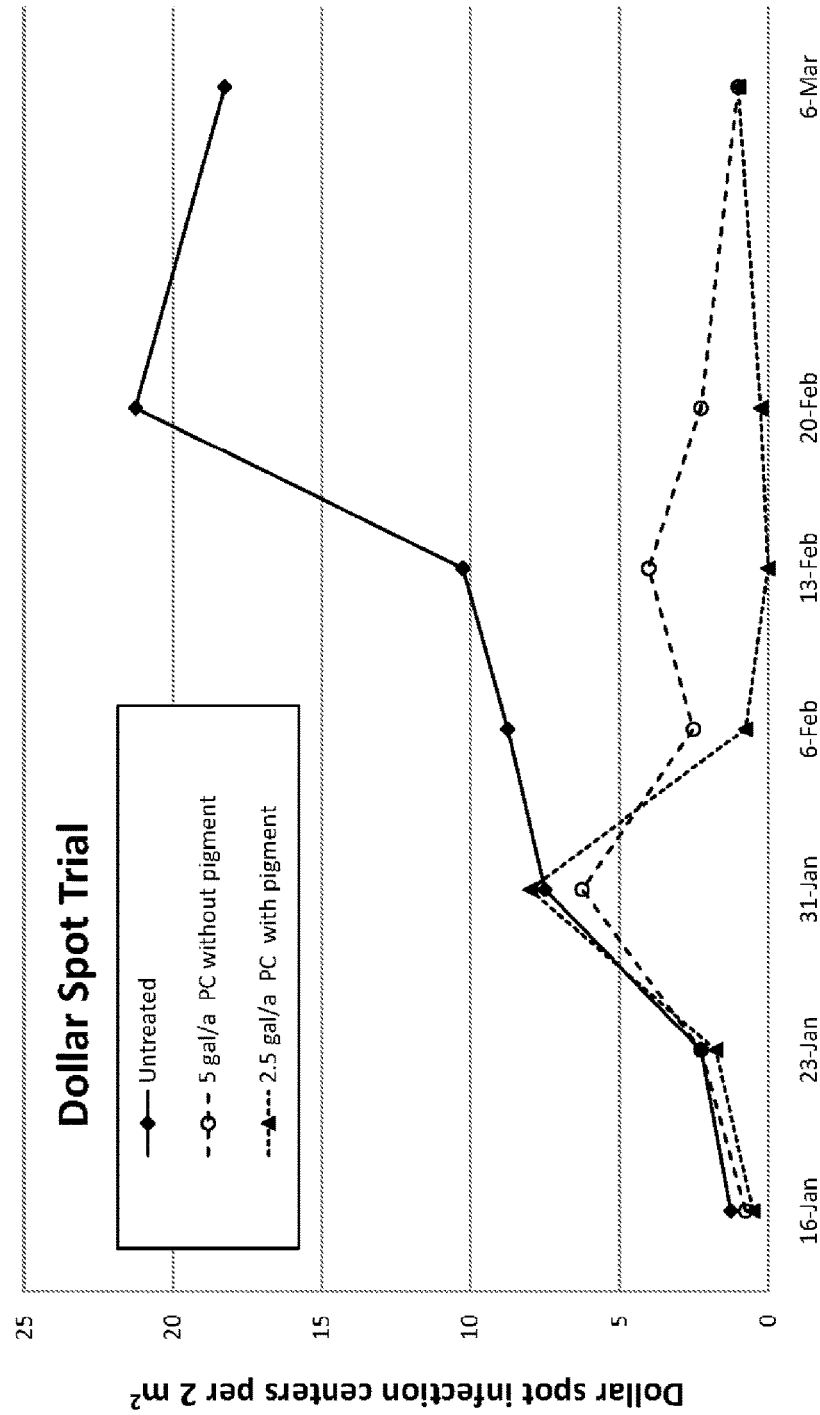
FIG. 4 is a graphical representation of the results of Example 10 showing the efficacy of weekly use of 2.5 gal/acre (non-aqueous portion) of 2-pack fungicide compared to an oil-in-water formulation without the addition of the polychlorinated Cu (II) phthalocyanine pigment, emulsifier and silicone additives applied weekly at 5 gal/acre (non-aqueous portion)

Having reference to FIG. 4, dollar spot counts were made throughout the 8 week period.

Conclusions:

Acceptable control of dollar spot was obtained through weekly use of 2.5 gal/acre (0.2 L/10 m$^2$) of the non-aqueous portion of 2-pack fungicide which represents approximately one half the amount required to achieve the same result using a formulation without the addition of the polychlorinated Cu (II) phthalocyanine pigment dispersion, emulsifier and silicone additives (5 gal/acre (0.5 L/100 m$^2$) of the non-aqueous portion, weekly).

Advantageously, the use of a lower treatment rate reduces the propensity for phytotoxicity which may be observed at high rate oil rates.

Example 11

Example 11 was performed using a formulation prepared according to Example 6.

Kentucky bluegrass was mowed three times per week at a cutting height of 2 inches. Applications of the 2-pack formulation were made at 14-day intervals beginning April 10. Assessment of Spring leaf spot or Melting-out disease was made using a "0 to 10" severity index, where 10 is equivalent to greater than 90% symptomatic turf area.

For the purposes of comparison to conventional treatment, DACONIL® ULTREX, available from Syngenta Crop Protection Canada, Inc. Guelph, Ontario, Canada, was used as a control.

Results

| Treatment | Application rate (oz/1000 ft$^2$) | Disease Severity | | | |
|---|---|---|---|---|---|
| | | 14-May | 22-May | 28-May | 4-Jun |
| Untreated | | 2.7 ab | 4.3a | 5.3 a | 6.7a |
| 2-pack | 21.75 | 0.0e | 0.3ef | 0.3ef | 0.3hi |
| DACONIL® Ultrex | 3.2 | 0.0e | 0.0f | 0.0f | 0.0i |
| LSD (P = 0.05) | | 1.45 | 0.96 | 1.38 | 1.28 |
| Std Deviation | | 0.89 | 0.59 | 0.85 | 0.78 |

Means in a row followed by the same letter are not significantly different (alpha = 0.05) using LSD test.

No phytotoxicity was observed in any treatment plot.

Conclusions:

The 2-Pack formulation, used at 7.5 gal/acre (0.7 L/100 m$^2$) of the non-aqueous portion) provided excellent disease control.

1-Pack Formulation

In another embodiment of the invention, Applicant has surprisingly found that pigment, such as polychlorinated Cu (II) phthalocyanine, can be prepared in a single, stable dispersion in an oil-based fungicidal composition, prior to dilution in water to form a sprayable dispersion. Thus, the user does not need to handle two separate components for preparing a stable fungicidal application.

More specifically, the pigment is dispersed in a compatible oil, such as a paraffinic oil or the same paraffinic oil as is used to provide the fungicidal properties as described in embodiments of the invention, for additional to the formulation. Use of specific silicone surfactant and emulsifier chemistries stabilizes the colorant in the oil-based composition.

In examples of the 1-pack formulation, polychlorinated Cu(II) phthalocyanine is dispersed in a paraffinic oil, such as N65DW (available from Petro-Canada) to provide about 18% polychlorinated CU(II) phthalocyanine (SUN-SPERSE® EXP 006-102, available from Sun Chemical Corp. Performance Pigments, Cincinnati, Ohio USA) prior to mixing with the remaining constituents.

In embodiments of the invention, the 1-pack formulation comprises silicone surfactant, emulsifier and polyethylene glycols which are selected to provide an intermolecular hydrophilic and lipophilic balance within the fungicidal formulation so as to substantially prevent the polychlorinated Cu(II) phthalocyanine from separating out of suspension during application to the turf grass.

Applicant believes that suitable silicone surfactants are those previously identified for the 2-pack formulation, as described in Formula (I). In embodiments of the invention the silicone surfactants are H-capped, CH$_3$-capped and COCH$_3$-capped trisiloxanes. In an embodiment of the invention, the silicone is an H-capped trisiloxane as shown below in Formula (III):

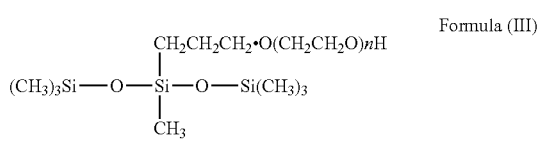

Formula (III)

Where: n=1-24, average n=8-10.

Suitable emulsifiers for the 1-Pack formulation are selected from the following:

Alcohol ethoxylates (natural and synthetic) including polyoxyethylene (4 to 7) lauryl ether (C12); polyoxyethylene (10) cetyl ether (C16); polyoxyethylene (2 to 11) C12-C15 alcohols; polyoxyethylene (3 to 9) 011-C14 alcohols; polyoxyethylene (9) C12-C14 alcohols;

Polymeric surfactants including graft copolymer such as polymethacrylic acid and acrylate with polyoxyethylene chains and random copolymers with ester and ether groups; and Sorbitan fatty acid esters including sorbitan tristearate and sorbitan trioleate.

The emulsifier is added to the formulation in a range of about 0.5 wt % to about 5 wt % in the non-aqueous portion of the formulation.

In embodiments of the invention, Applicant has noted that the silicone surfactants used typically comprise 10-30% polyethylene glycols (PEG) according to Formula (IV) shown below.

   Formula (IV)

Where:
$R_1$=H or $CH_2$=CH—$CH_2$ or $COCH_3$
$R_2$=H or $CH_2$=CH—$CH_2$ or $COCH_3$
$n \geq 1$ In embodiments of the invention, the PEG has a low molecular weight, typically about 300 to about 1500 Daltons. In embodiments of the invention, the PEG is a low molecular weight polyethylene glycol allyl ether. In embodiments of the invention, the PEG is a low molecular weight polyethylene glycol mono-allyl ether having an average molecular weight of from about 300 to about 600 Daltons and having from 1 to 20 moles of ethylene glycol with an average ethoxylation (EO) of 8 to 10.

Examples 12 to 14—1-Pack Formulations

Example 12

28 wt % SUNSPERSE® EXP 006-102 containing 18 wt % polychlorinated Cu(II) phthalocyanine, dispersed in N65DW;

2 wt % silicone surfactant according to Formula (I) where: m=1, n=0, X=1-24 (average 8-10) and R=H; and PEG according to Formula (IV) where: $R_1$=$CH_2$=CH—$CH_2$, $R_2$=H and n=1-20 with an average n=8 (Lambent MFF199);

2 wt % polyoxyethylene (11) $C_{16-18}$ alcohols such as LUTENSOL® AT11 available from BASF; and 68 wt % N65DW.

Example 13

28 wt % SUNSPERSE® EXP 006-102 containing 18 wt % polychlorinated Cu(II) phthalocyanine, dispersed in N65DW;

2 wt % silicone surfactant according to Formula (I) where: m=1, n=0, X=1-24 (average 8-10) and R=H; and PEG according to Formula (IV) where: $R_1$=$CH_2$=CH—$CH_2$, $R_2$=H and n=1-20 with an average n=8 (Lambent MFF199);

2 wt % sorbitan tristearate such as SPAN65 available from Uniqema or S-MAZ® 65K available from BASF; and 68 wt % N65DW.

Example 14

28 wt % SUNSPERSE® EXP 006-102 containing 18 wt % polychlorinated Cu(II) phthalocyanine, dispersed in N65DW;

1.8 wt % silicone surfactant as described in Formula (I) where m=1, n=0, X=1-24 (average 8-10) and R=$COCH_3$, and Polyethylene Glycols as described in Formula (IV) where $R_1$=$CH_2$=CH—$CH_2$ or $COCH_3$, $R_2$=$COCH_3$ (SYLGARD® 309, available from Dow Corning, USA)

0.2% Polyethylene Glycols as described in Formula (IV) where $R_1$=$CH_2$=CH—$CH_2$, $R_2$=H (Polyglykol A500, available from Clariant);

2 wt % polyoxyethylene (11) $C_{16-18}$ alcohols, such as LUTENSOL® AT11 available from BASF; and 68 wt % N65DW.

The formulations disclosed in Examples 12-14 were further diluted to 6% in water prior to application to the turfgrass. The resulting oil-in-water formulations comprised:

about 5 wt % paraffinic oil;
about 0.12 wt % emulsifier;
about 0.3 wt % polychlorinated Cu(II) phthalocyanine;
about 0.1 wt % silicone surfactant;
about 0.01-0.03 wt % polyethylene glycol; and
the balance being water.

The resulting oil-in-water emulsion/pigment dispersions were found to be stable until applied, typically within one day and can be applied to turfgrass. The oil-in-water emulsions were applied at a conventional total spray volume rate of about 50 gal/acre (4.7 L/100 m$^2$) to about 100 gal/acre (9.3 L/100 m$^2$).

Examples 15-17

Additional testing was performed to determine the stability of 1-pack formulations without the presence of silicone surfactant and/or PEG.

In Examples 15-17, the formulations were further diluted to 6% in water to form the oil-in-water emulsion prior to application to turfgrass.

Example 15

A 1-pack formulation was prepared with neither silicone surfactant nor PEG according to the following formula:

28 wt % SUNSPERSE® EXP 006-102 containing 18 wt % polychlorinated Cu(II) phthalocyanine, dispersed in N65DW;

2 wt % polyoxyethylene (11) $C_{16-18}$ alcohols such as LUTENSOL® AT11 available from BASF; and

70% N65DW.

Example 16

A 1-pack formulation was prepared with insufficient PEG according to the following formula:

28 wt % SUNSPERSE® EXP 006-102 containing 18 wt % polychlorinated Cu(II) phthalocyanine, dispersed in N65DW;

2 wt % silicone surfactant as described in Formula (I) where m=1, n=0, X=1-24 (average 8-10) and R=H (SILTECH® SILSURF® A008-UP);

2 wt % polyoxyethylene (11) $C_{16-18}$ alcohols such as LUTENSOL® AT11 available from BASF; and

68% N65DW.

Example 17

A 1-pack formulation was prepared without silicone surfactant according to the following formula:

28 wt % SUNSPERSE® EXP 006-102 containing 18 wt % polychlorinated Cu(II) phthalocyanine, dispersed in N65DW;

2 wt % Polyethylene Glycols as described in Formula (IV) where $R_1$=$CH_2$=CH—$CH_2$, $R_2$=H (Polyglykol A500, available from Clariant);

2 wt % polyoxyethylene $(11)^C_{16-18}$ alcohols such as LUTENSOL® AT11 available from BASF; and

68% N65DW.

Results:

The pigment aggregated and fell out of suspension in all of the formulations tested in Examples 15-17, rendering the formulations unusable.

Conclusions:

As shown in Examples 12-17, without both silicone surfactant and sufficient amounts of PEG, the resulting 1-pack formulations, diluted to form oil-in-water emulsions, are not stable and are therefore not usable for turf application.

As demonstrated in Examples 12-17, the presence of silicone surfactants and polyethylene glycols improve the stability and dispersibility of the 1-Pack formulation resulting in a commercially viable fungicidal dispersant for turf application and management of disease therein.

Example 18

Embodiments of the 1-pack and 2-pack formulations, according to the invention, and a conventional fungicide, DACONIL® Ultrex, were used to treat dollar Spot on *Poa Trivialis* (rough stalk bluegrass) overseeded Bermudagrass plot cut at putting green height. As with Example 10, the formulations were applied with a $CO_2$ backpack boom sprayer calibrated to deliver products in 2 gallons of water per 1000 sq ft (8 L 1100 m²) through two 8003 TEEJET® flat fan nozzles.

The plots were divided into 4 blocks and treatments were assigned in a randomized complete block design. The plot was inoculated with 1 L of wheat seed infested with *Sclerotinia homoeocarpa*. The formulations were applied biweekly for 8 weeks.

Figure 5:
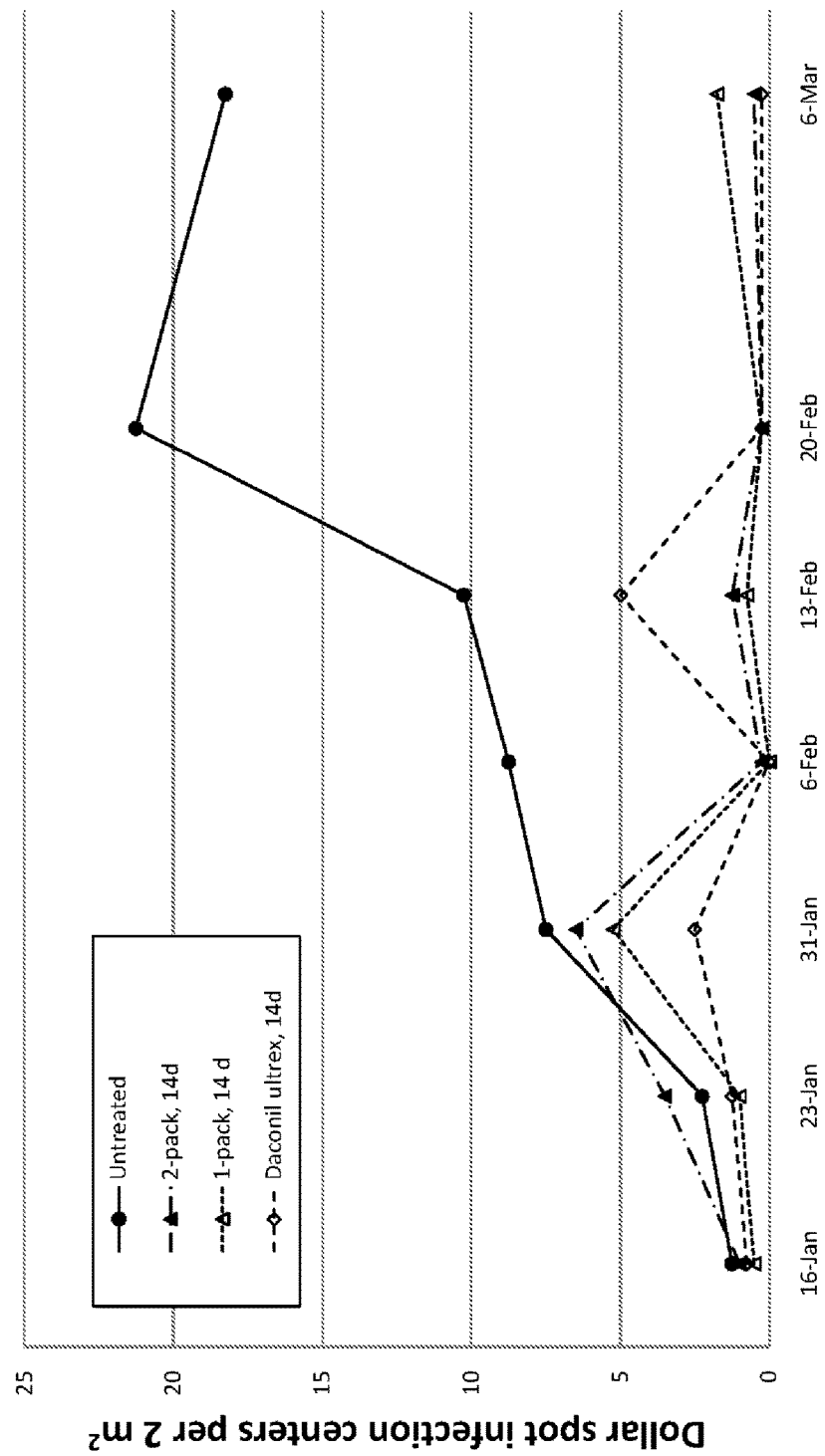
FIG. 5 is a graphical representation of the results of Example 18 comparing the efficacy of the 2-pack formulation, a 1-pack formulation and convention chemical fungicide DACONIL® Ultrex for treating turfgrass infected with Dollar Spot disease.

As shown in FIG. 5, dollar spot counts were made throughout the 8 week period.

Conclusions:

Both the 1-pack and 2-pack formulations had substantially the same efficacy as the DACONIL® Ultrex.

Example 19

A 2-Pack formulation was prepared according to Example 6 an applied on a fairway and an area of rough at the Saginaw Golf Course in Cambridge, Ontario, Canada for an 8 week period using a 14-day application interval.

At the end of 8 weeks, core samples of the treated and untreated areas were obtained to compare root development.

Results

Figure 6:
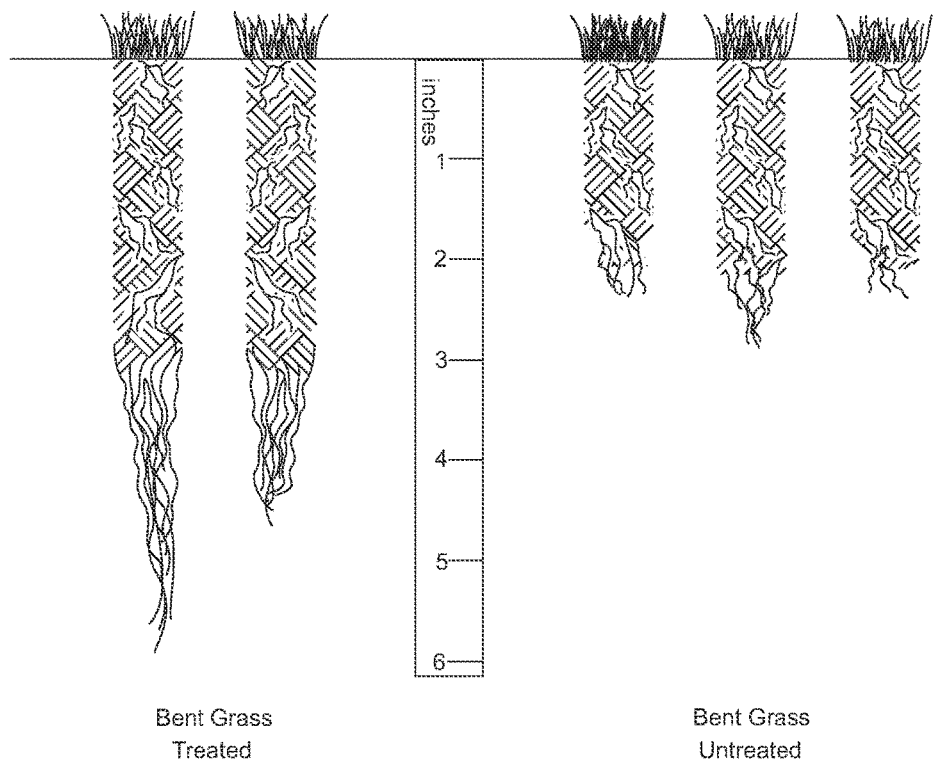
FIG. 6 is a picture of increased root length as a result of the application of a 2-Pack formulation prepared according to Example 6 when applied to a golf course fairway.

As shown in FIG. 6, the grass on the treated areas (left) was much denser and healthier than on the untreated areas (right). Further, the treated areas had a darker green color than the untreated areas.

It was found that the roots of the bentgrass on the treated area were longer by approximately twice the length of the roots of the untreated bentgrass. Further, the roots were observed to be denser than the roots of untreated bentgrass.

Conclusions:

The 2-Pack and 1-Pack formulations promote the growth of bentgrass and bluegrass.

Example 20

Figure 7:
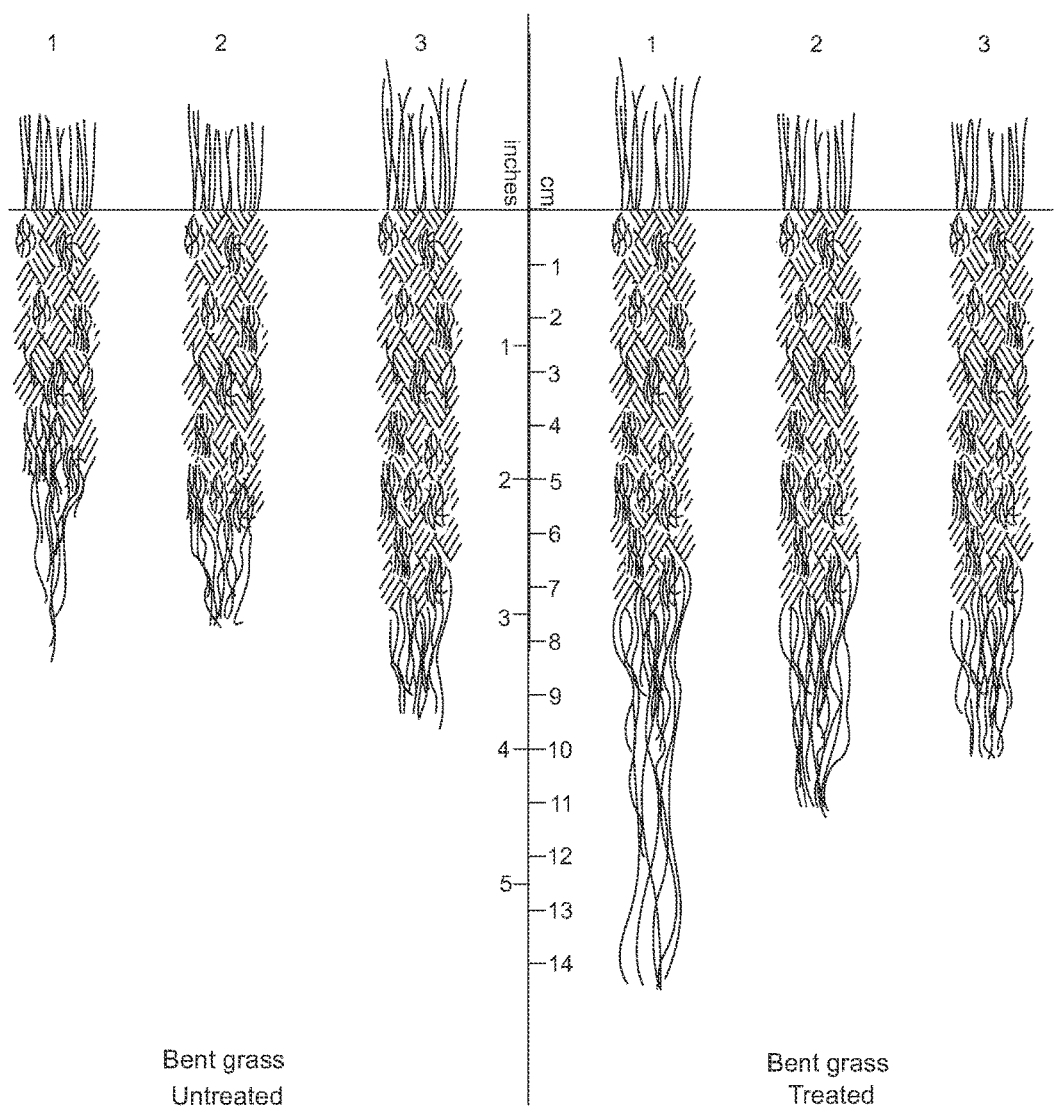
FIG. 7 is a picture of increased root length as a result of the application of a 2-Pack formulation, prepared according to Example 6, to areas of bentgrass.
Figure 8:
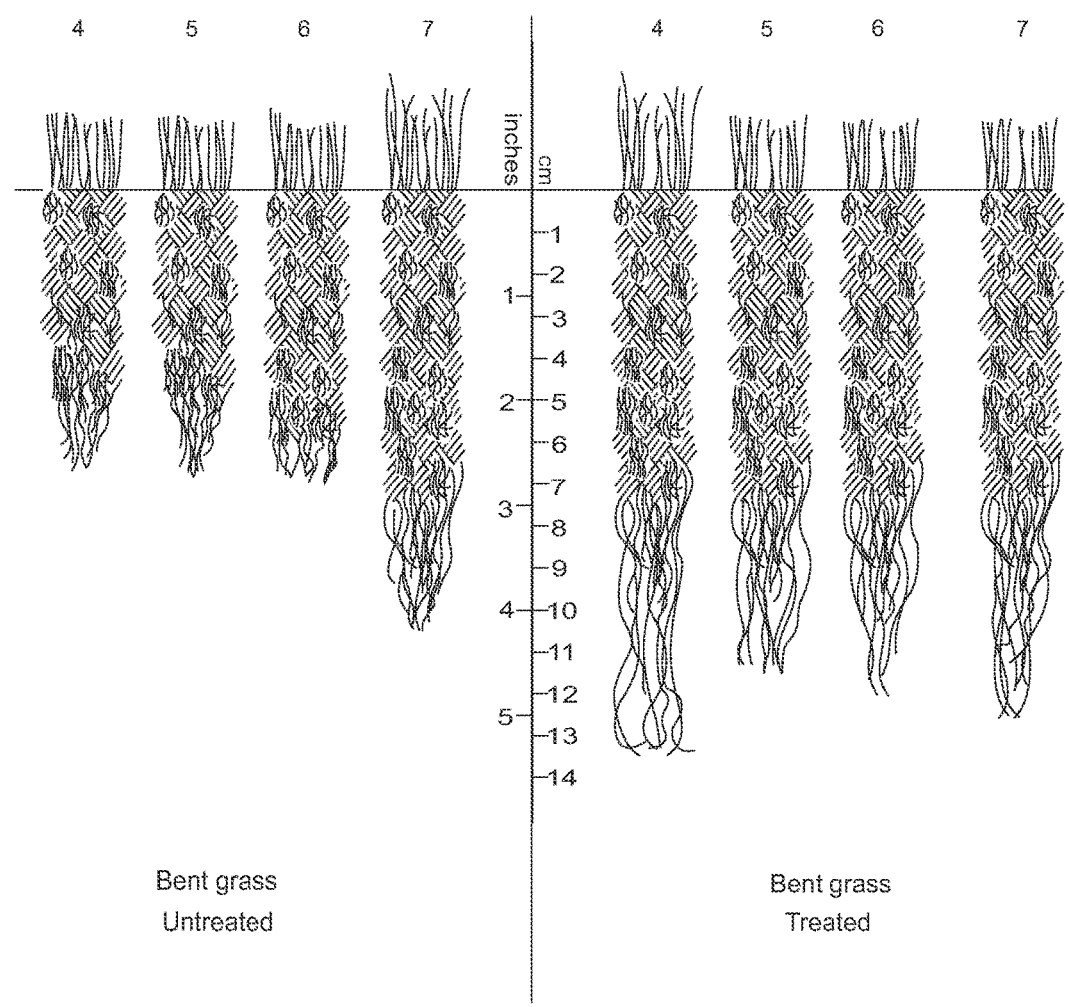
FIG. 8 is a picture of increased root length as a result of the application of a 2-Pack formulation, prepared according to Example 6, to areas of bentgrass.

Having reference to FIGS. 7 and 8, areas of bentgrass were treated using a 2-Pack formulation prepared according to Example 6. Seven (7) core samples were randomly taken from treated areas and from untreated areas for comparison. The core samples were soaked overnight in water in a glass tray. Subsequently, soil from the roots was washed away with water to reveal the root structure, as shown in FIGS. 7 and 8 and summarized in Table A below.

Results

TABLE A

| Core sample # | Untreated root length (inches) | Treated root length (inches) |
|---|---|---|
| 1 | 3.5 | 5.5 |
| 2 | 3.0 | 4.5 |
| 3 | 3.75 | 4.0 |
| 4 | 2.75 | 5.25 |
| 5 | 2.75 | 4.5 |
| 6 | 2.75 | 4.75 |
| 7 | 4.25 | 4.75 |
| Average | 3.25 | 4.75 |

Conclusions:

On the average, the root length of the treated bentgrass is approximately 50% longer than that of the untreated bentgrass. Further it was noted that the root mass was considerably greater for the treated bentgrass.

Enhanced Formulation

Applicant has determined that embodiments of the present invention have a surprising synergistic effect when mixed with some conventional systemic chemical fungicides selected from the group consisting of demethylation inhibitors (such as propiconazole), methyl benzimidazole carbamate (such as thiophanate-methyl) and dicarboximide (such as iprodione). As an example, a suitable propiconazole fungicide is BANNER MAXX™ (available from Syngenta Crop Protection Canada, Inc. Guelph, Ontario, Canada), a thiophanate-methyl fungicide is Cleary 3336™ (available from Cleary Chemical Corporation, Dayton, N.J., USA) and an iprodione fungicide is ROVRAL® Green (available from Bayer Environmental Science-Canada, Guelph, Ontario, Canada).

Applicant has found however that, despite predictions to the contrary, the synergistic effect was not observed with all conventional chemical fungicides, such as some contact fungicides, one of which was chlorothalonil (such as DACONIL® Ultrex, available from Syngenta Crop Protection Canada, Inc. Guelph, Ontario, Canada).

As shown in the following additional examples for treatment of Dollar Spot, snow moulds and gray leaf spot, mixing an embodiment of the present invention at half the predicated recommended label rate in equal parts with certain conventional chemical fungicides at half the amount of the label rate resulted in an equivalent or improved efficacy of the mixture when compared to each of the fungicides used alone at full label rate.

As one of skill would understand and as taught by Burpee and Latin, Plant Disease Vol. 92 No. 4, April 2008, pp 601-606, knowing that the efficacy of fungicides is not additive, the addition of half the label rate of each of the two fungicidal formulations would not conventionally be thought to result in high efficacy. Surprisingly this was not the case with embodiments of the present invention. Mixtures of formulations of the present invention and certain conventional chemical fungicides, at rates not thought to be useful, resulted synergistically in a highly efficacious formulation.

Applicant believes that the amount of formulations according to embodiments of the invention can be reduced to a range from about 25% to about 75% of the amount used if used alone, when mixed with the conventional chemical fungicide, also reduced to from about 25% to about 75% of the recommended label rate.

Examples 21 and 22

Examples 21 and 22 illustrate results of use of the 1-pack formulation, the two pack formulation and the enhanced formulation on the treatment of Dollar Spot on *Poa Trivialis* (rough stalk bluegrass) cut at putting green height.

Example 21

Figure 9A:
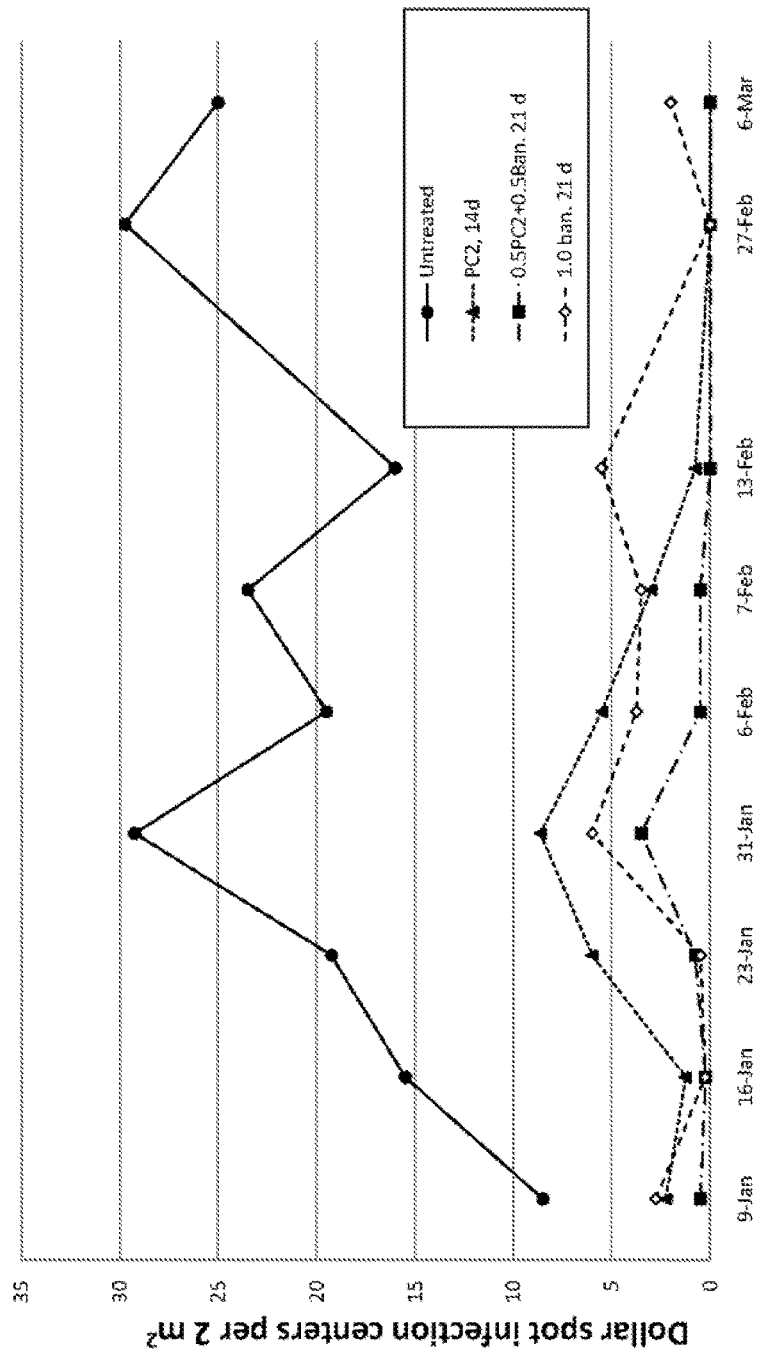
FIG. 9A is a graphical representation of the results of Example 21 comparing the efficacy of a 2-pack formulation and a 2-pack formulation tank mixed at 50:50 with chemical fungicide BANNER MAXX™ for treating turf infected with Dollar Spot disease.
Figure 9B:
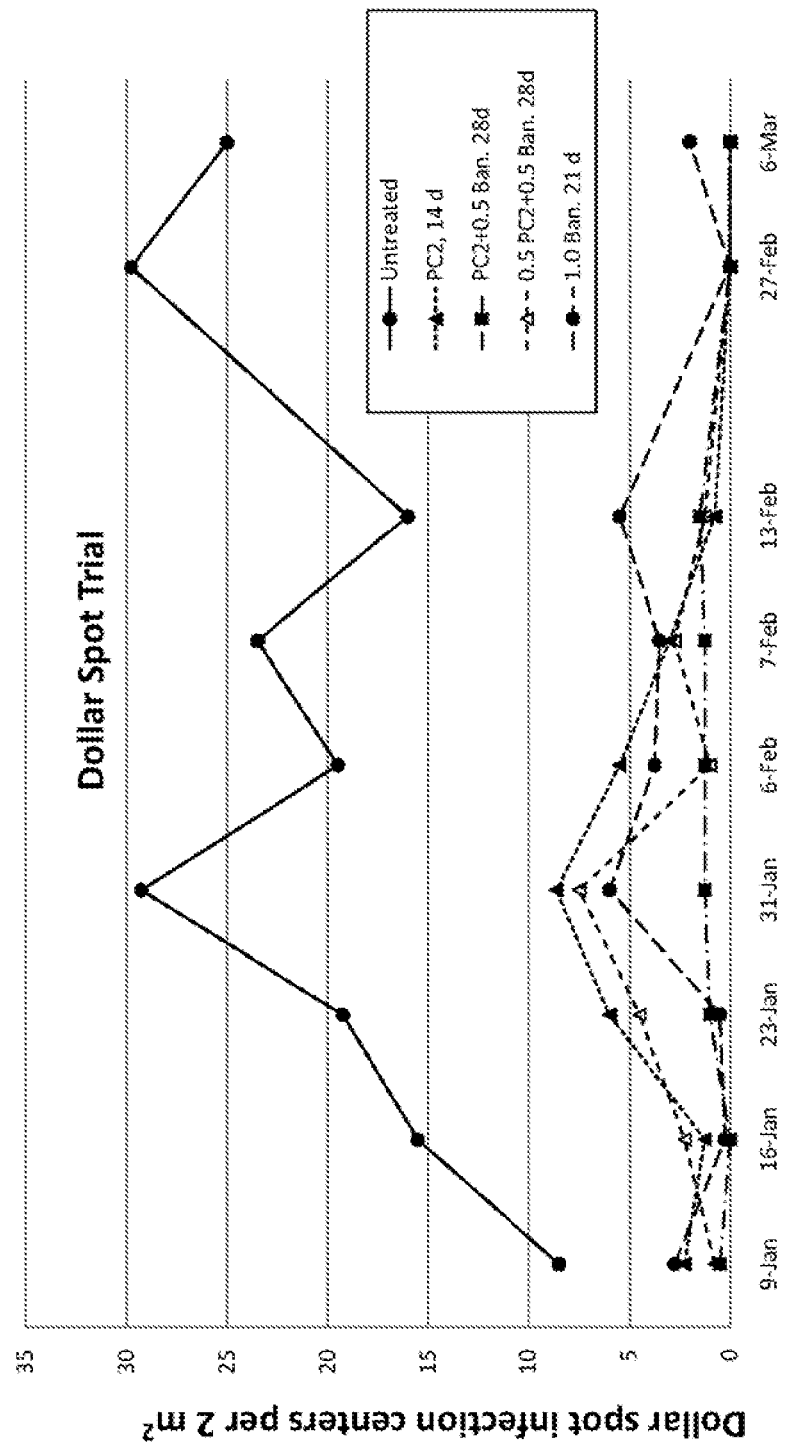
FIG. 9B is a graphical representation of the results of Example 21 showing a synergistic effect of a 2-pack formulation tank mixed at 50:50 with chemical fungicide BANNER MAXX™ compared to the 2-pack formulation alone for treating turf infected with Dollar Spot disease, the residue period extending from 21 days to 28 days.

Having reference to FIGS. 9A and 9B, the 2-pack formulation was tank mixed at 50:50 with chemical fungicide BANNER MAXX™ and applied to turf infected with dollar spot disease.

The mixture of the 2-pack fungicide and the chemical fungicide exhibited a synergistic effect compared to using either of the fungicides alone. As shown in FIG. 9B, the residue period can be extended from 21 days to 28 days.

Example 22

Figure 10:
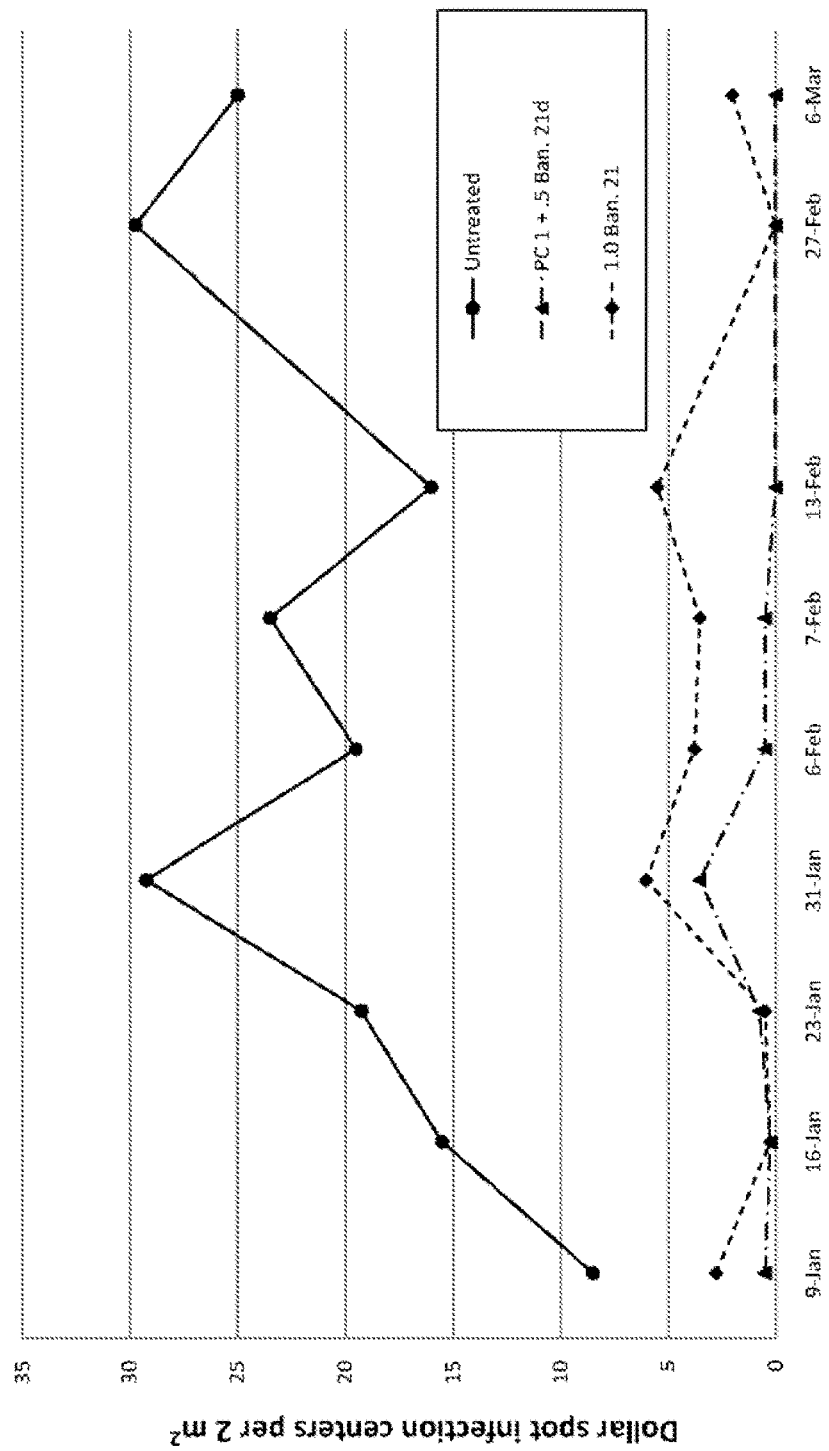
FIG. 10 is a graphical representation of the results of Example 22 showing a synergistic effect of a 1-pack formulation tank mixed 50:50 with chemical fungicide BANNER MAXX™ compared to the 1-pack formulation alone for treating turf infected with dollar spot disease.

Having reference to FIG. 10, the 1-pack formulation was tank mixed 50:50 with chemical fungicide BANNER MAXX™ and applied to turf infected with dollar spot disease.

The 1-pack formulation with the addition of chemical fungicide exhibited a synergistic effect when compared to use of the 1-pack formulation or BANNER MAXX™ alone, when applied at the full label rate.

Examples 23-25

Embodiments of the invention were mixed 50:50 with conventional chemical fungicide BANNER MAXX™ to form an enhanced formulation and were applied to creeping bentgrass (*Agrostis stolonifera*) at fairway height which was infected with a variety of snowmolds.

An enhanced formulation containing the 2-pack formulation and chemical fungicide was compared to use of the fungicides alone. BANNER MAXX™ was applied at 50% the recommended label rate for comparison to the enhanced formulation.

Example 23

Figure 11:
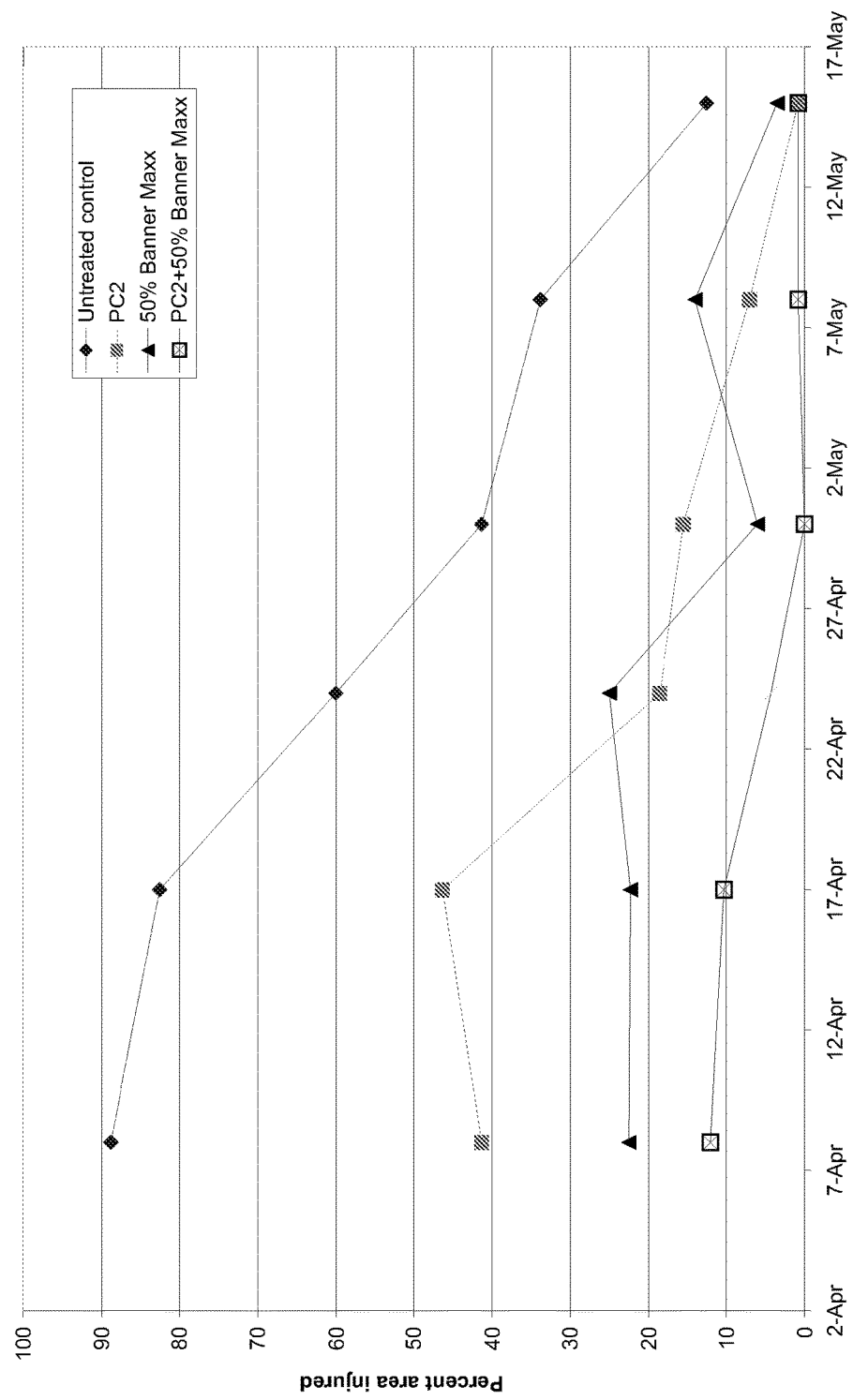
FIG. 11 is a graphical representation of the results of Example 23 illustrating the effectiveness of a 2-pack formulation with 50% of the recommended label rate of BANNER MAXX™ compared to the 2-pack formulation alone, 50% of the recommended label rate of BANNER MAXX™ alone and an untreated control for treating turf infected with *Typhula ishikariensis*.

As shown in FIG. 11, the effectiveness of the enhanced formulation was compared to the 2-pack formulation, 50% of the recommended label rate of BANNER MAXX™ alone and an untreated control for treating turf infected with *Typhula ishikariensis*.

Example 24

Figure 12:
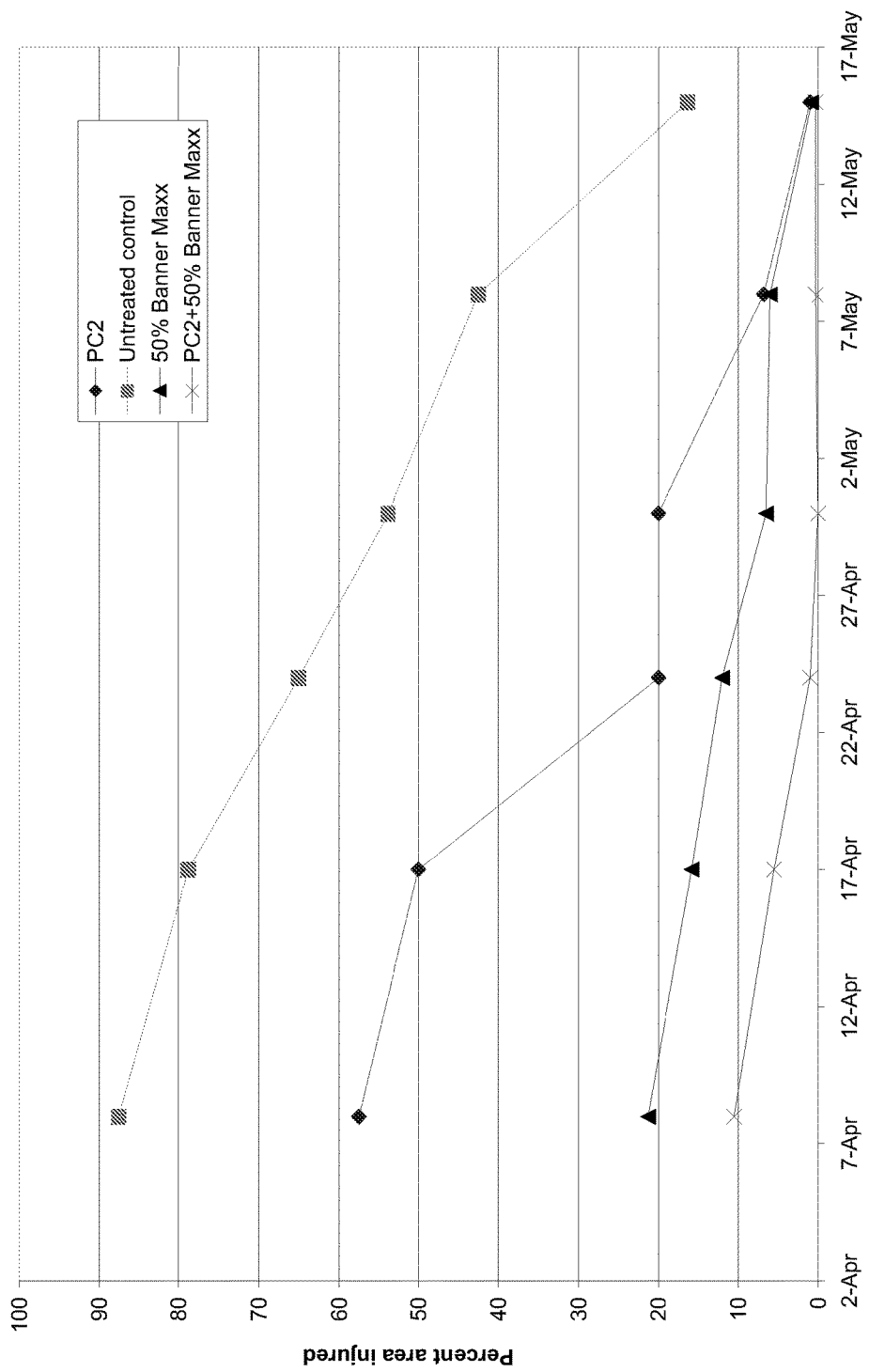
FIG. 12 is a graphical representation of the results of Example 24 illustrating the effectiveness of a 2-pack formulation with 50% of the recommended label rate of BANNER MAXX™ compared to the 2-pack formulation alone, 50% of the recommended label rate of BANNER MAXX™ alone and an untreated control for treating turf infected with *Typhula incarnata*.

As shown in FIG. 12, the effectiveness of the enhanced formulation was compared to the 2-pack formulation, 50% of the recommended label rate of BANNER MAXX™ alone and an untreated control for treating turf infected with *Typhula incarnata*.

Example 25

Figure 13:
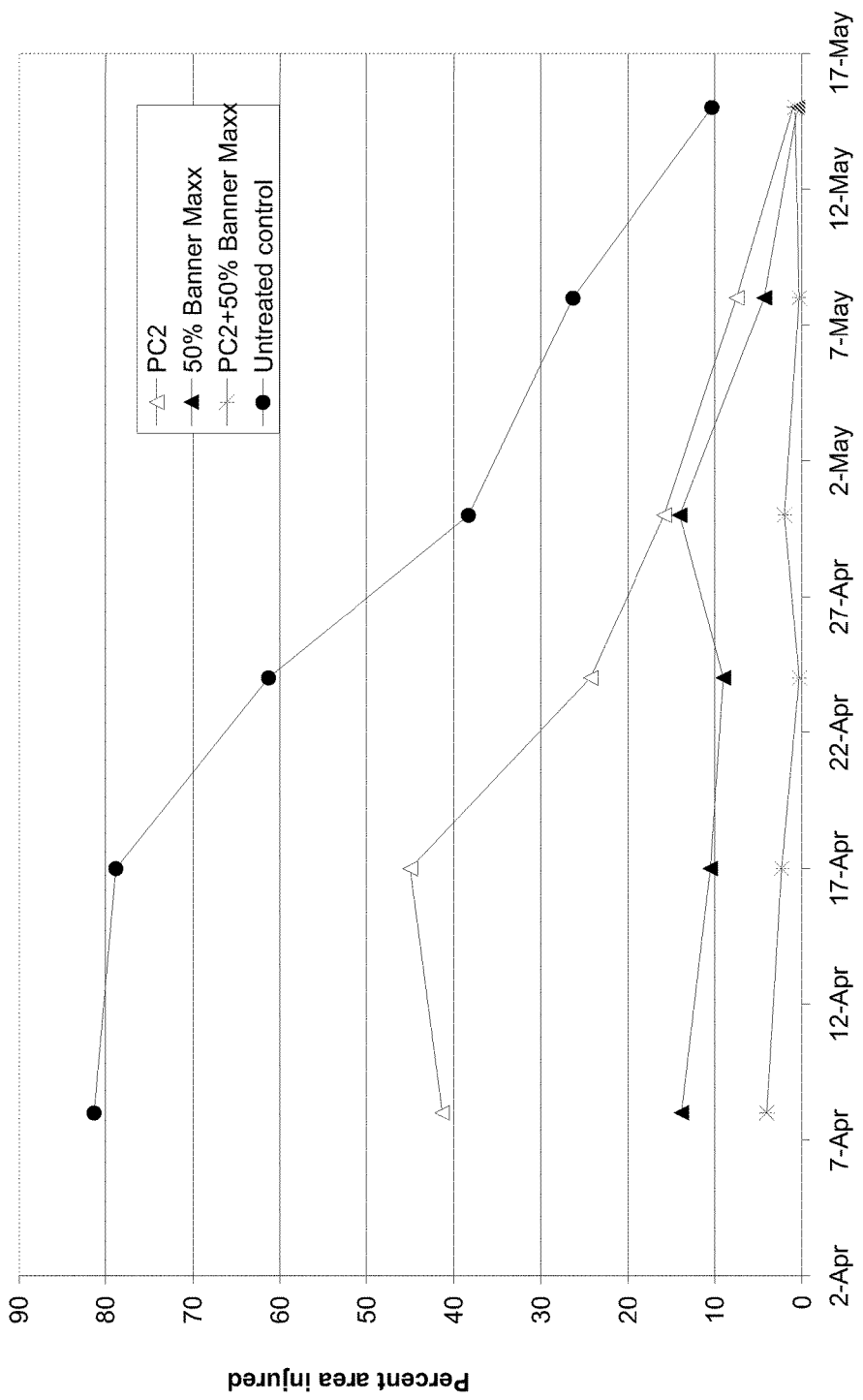
FIG. 13 is a graphical representation of the results of Example 25 illustrating the effectiveness of a 2-pack formulation with 50% of the recommended label rate of BANNER MAXX™ compared to the 2-pack formulation alone, 50% of the recommended label rate of BANNER MAXX™ alone and an untreated control for treating turf infected with *Microdochium nivale*.

As shown in FIG. 13, the effectiveness of the enhanced formulation was compared to the 2-pack formulation, 50% of the recommended label rate of BANNER MAXX™ alone and an untreated control for treating turf infected with *Microdochium nivale*.

Conclusions:

It is clear from Examples 23-25 that use of the enhanced formulation comprising 50% of the recommended rate of an embodiment of the invention and 50% of the recommended label rate of BANNER MAXX™ is as effective, or more effective, than using either the 2-pack formulation or the chemical fungicide alone.

Example 26

A 2-Pack formulation was prepared according to Example 6 using half the recommended rate (i.e. 232.5 ml per 100 m$^2$ for the non-aqueous portion) and was mixed with a commercial fungicide ROVRAL® Green GT (available from Bayer Environmental Science-Canada, Guelph, Ontario, Canada) at 50% the recommended label rate (i.e., applied at 125 ml per 100 m$^2$) to form the enhanced formulation.

The enhanced formulation was applied to creeping bentgrass (*Agrostis stolonifera*) cut to greens height for the control of *Fusarium* Patch disease. ROVRAL® Green GT was also applied alone at 50% the recommended rate ((i.e., applied at 125 ml per 100 m$^2$) for comparison.

The treatments were applied over a 6-week period and disease was monitored weekly.

Figure 14:
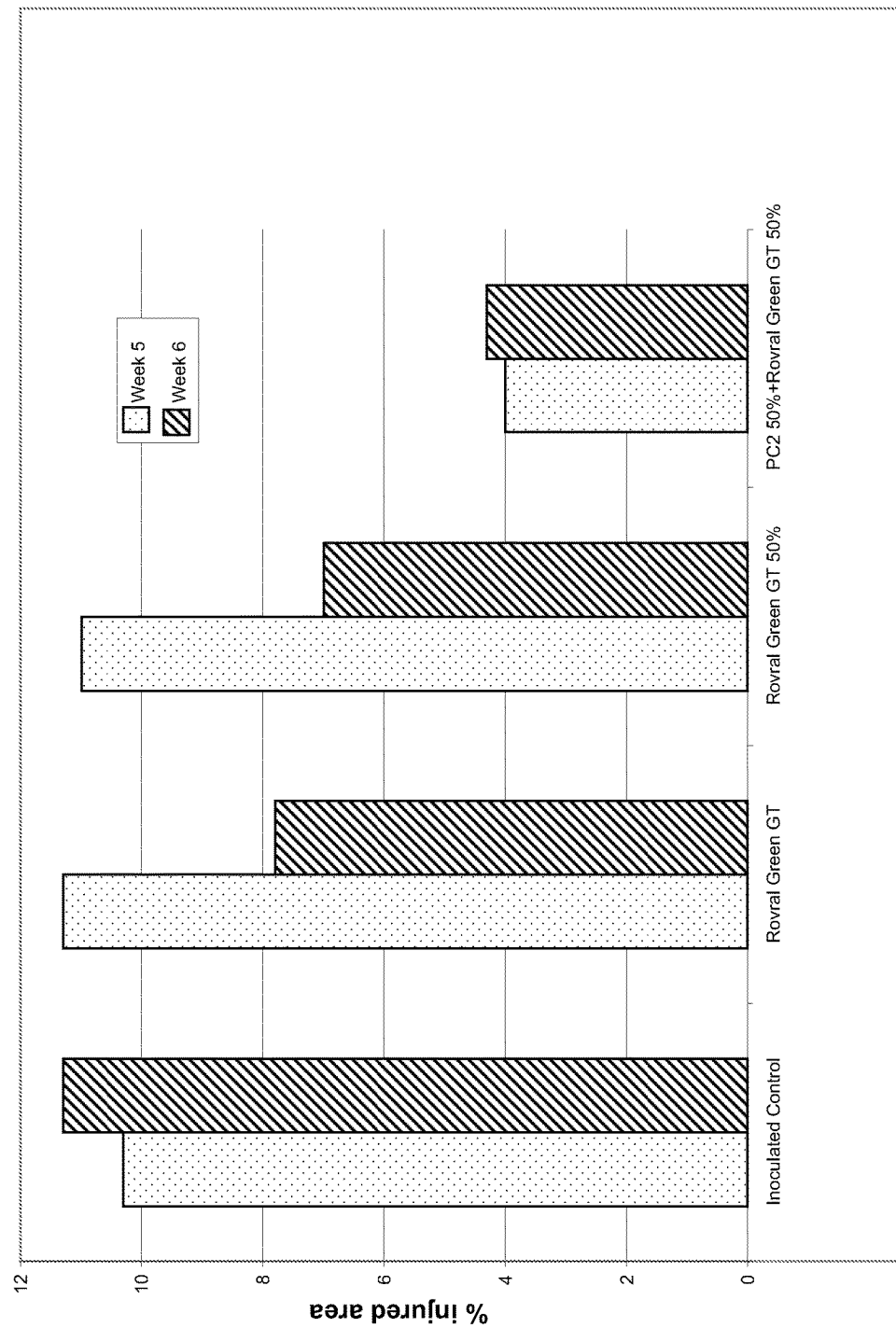
FIG. 14 is a graphical representation of the results of Example 26 comparing the efficacy of a 2-pack formulation enhanced with 50% of the recommended label rate of ROVRAL® Green GT to ROVRAL® Green GT at full label rate alone and ROVRAL® Green GT applied alone at 50% of the recommended label rate for the control of *Fusarium* Patch disease on bentgrass.

Conclusions:

As shown in FIG. 14, the enhanced formulation ("PC2 50%+ROVRAL® Green GT 50%") provided significant suppression of injury by *Fusarium* Patch disease.

Example 27

One half (50%) of the recommended rate of a 2-Pack formulation (i.e., at 2.5 gal per acre of the non-aqueous portion), prepared according to Example 6, was mixed 50:50 with a conventional chemical fungicide Cleary 3336™ Plus at 50% the recommended rate (i.e., at 2 oz per 1000 ft$^2$).

The enhanced formulation (PC2, ½ rate+Cleary 3336™ Plus, ½ rate), as well as the individual formulations at full rate and at half rate, were applied to perennial ryegrass cut to fairway height for control of Gray Leaf Spot disease.

Figure 15:
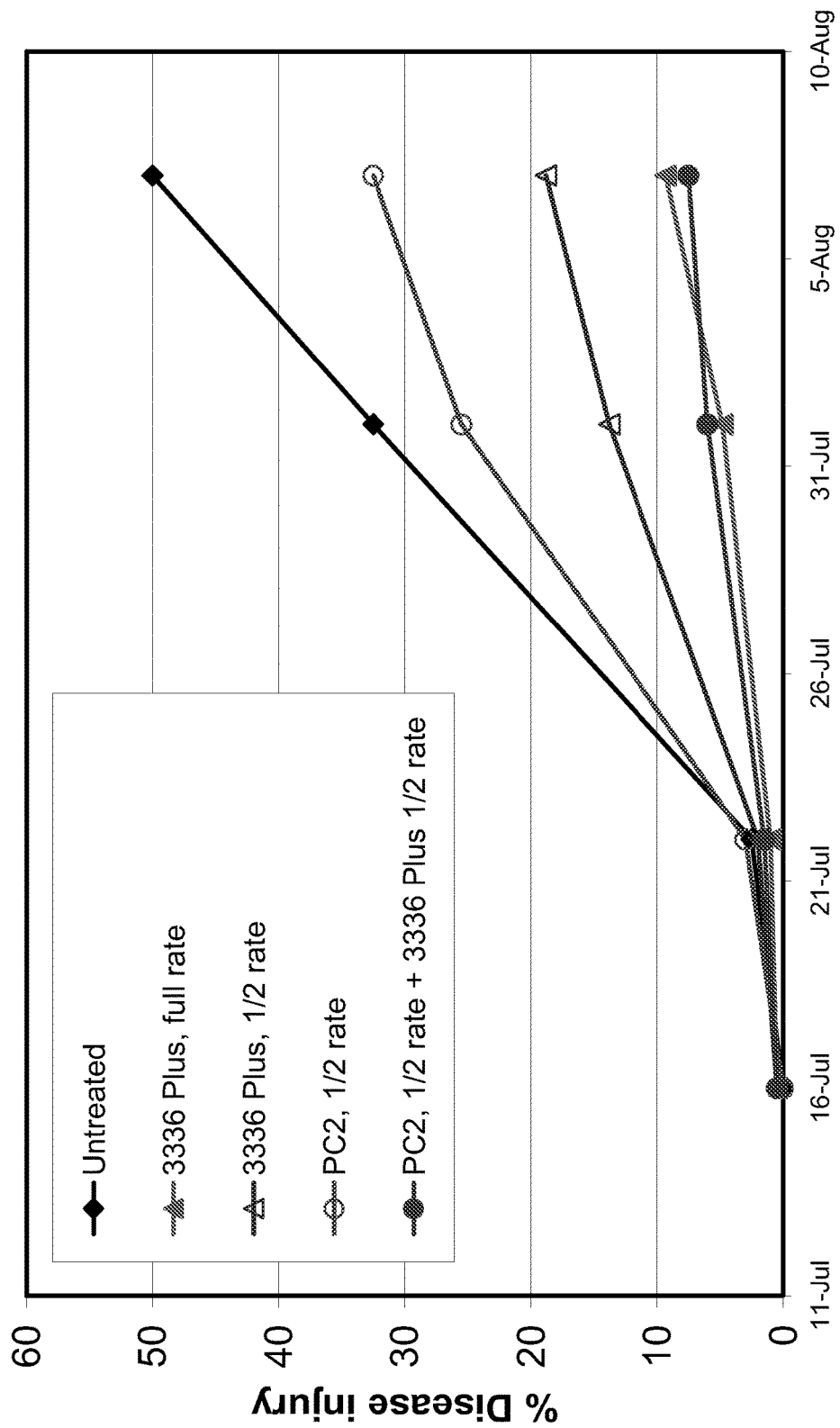
FIG. 15 is a graphical representation of the results of Example 27 comparing the efficacy of a 2-Pack formulation prepared according to Example 6 and applied at the full rate, conventional chemical fungicide Cleary 3336™ Plus at the full recommended label rate, the 2-pack formulation mixed 50:50 with Cleary 3336™ Plus, the 2-pack formulation alone at 50% of the recommended rate, and Cleary 3336™ Plus alone at 50% the recommended label rate, when applied to perennial ryegrass for control of Gray Leaf Spot disease.

Conclusions:

As shown in FIG. 15, the enhanced formulation provided excellent control of Gray Leaf Spot disease on Ryegrass.

Synergistic Effect of the Oil/Emulsion and Pigment Dispersion

Example 28

Figure 16:
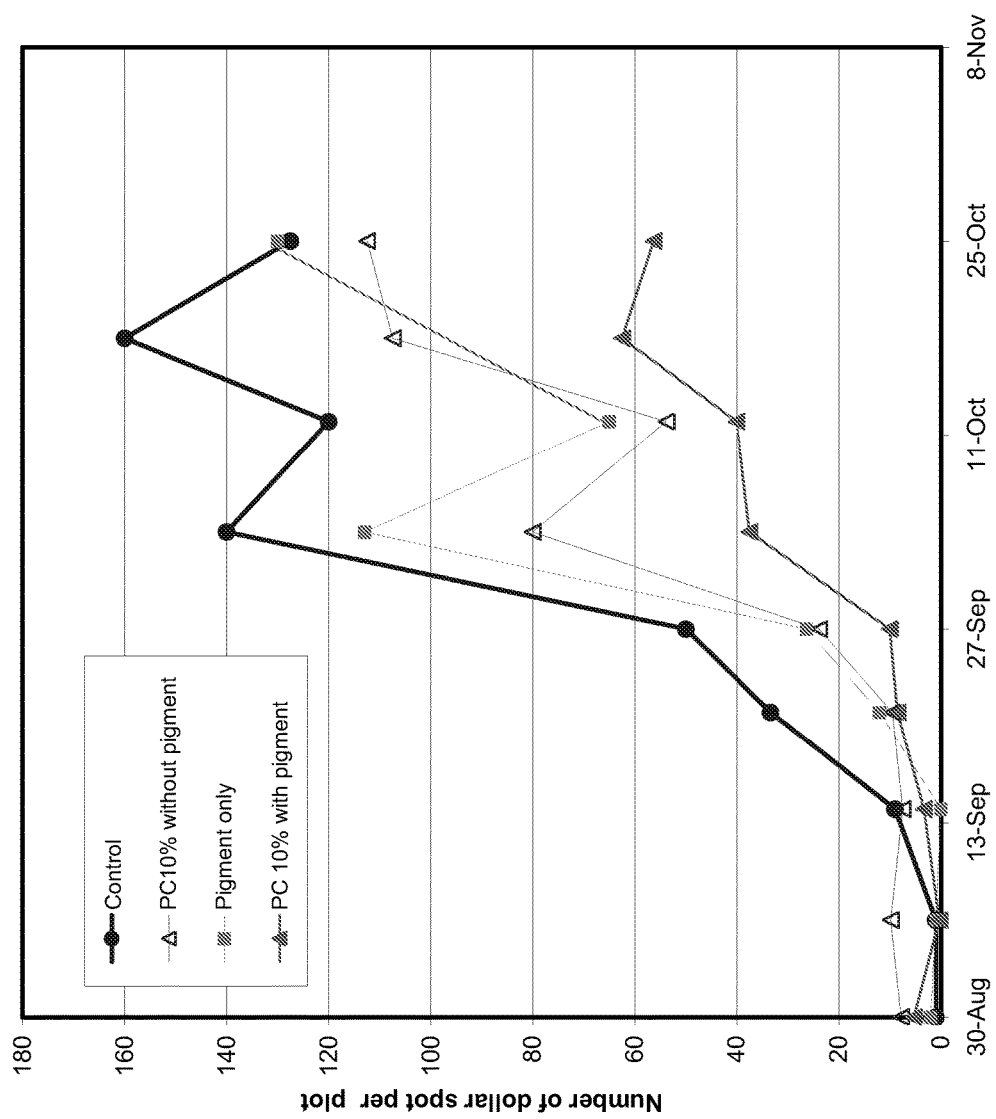
FIG. 16 is a graphical representation of the results of Example 28 illustrating a synergistic effect of the addition polychlorinated Cu(II) phthalocyanine when compared to oil/emulsifier alone and pigment alone, when compared to an untreated control.

As shown in FIG. 16, Applicant believes that in all formulations according to embodiments of the invention, the addition of the polychlorinated Cu(II) phthalocyanine has a synergistic effect when compared to oil/emulsifier alone or pigment alone, when compared to an untreated control.

Turf infected with Dollar Spot disease was treated with 10% oil/emulsifier alone, 0.5% SUNSPERSE® Green 7 alone and an embodiment of the invention comprising both 10% oil/emulsifier and 0.5% SUNSPERSE® Green 7.

Conclusions:

Clearly, it appears that addition of pigment to the fungicidal oil component enhances the fungicidal properties of the dispersion.

Use of Embodiments of the Invention for Controlling Additional Pests in Turfgrass Example 29

Fall Armyworms

The efficacy of an embodiment of the 2-pack formulation against different larval stages of fall armyworms (*Spodoptera frugiperda*) was determined under laboratory conditions. Embodiments of the invention were compared to a conventional pesticide Cyfluthrin.

Methods:
1) Larvae were obtained from Benzon Research Inc.
2) 5 larvae/container and 3 containers=1 replication
3) Treatments=1) Control
    2) 2-pack formulation at 5% dilution
    3) Cyfluthrin (insecticide), AI=0.75%, 3 fl oz/gal H₂O (22 mL/L)
4) Container=760 ml plastic bowl with lid containing moist filter paper on bottom and grass clippings
5) St. Augustinegrass clippings dipped into respective fungicide treatment, drained to dry and put into container
6) Hold 4 days at 25° C. and measure survival
7) 7 replications of small larvae (2-10 mm) tested
8) 6 replications of medium larvae (11-20 mm) tested
9) 6 replications of large larvae (21-30 mm) tested
10) Statistical analysis=Least Significant Difference (LSD) test Results:

| | Fall army worms | | |
|---|---|---|---|
| | | Mean survival[a] | |
| Larvae | control | Cyfluthrin | 2-pack formulation |
| Small | 3.86 A | 0 B | 0.43 B |
| Medium | 3.50 A | 0 B | 1.17 B |
| Large | 3.00 A | 0 B | 2.50 A |

[a]Means in a row followed by the same letter are not significantly different (alpha = 0.05) using LSD test.

Conclusions:

The data indicates that embodiments of the 2-pack formulation are effective to kill small and medium larvae of fall army worms.

Tropical Sod Webworms

Similar testing was conducted to determine the efficacy of embodiments of the 2-pack formulation to kill all sizes larvae (small, medium and large) of tropical sod webworms.

| | Sodweb worms | | |
|---|---|---|---|
| | | Mean survival[a] | |
| Larvae | control | Cyfluthrin | PC |
| Small | 3.0 A | 0 B | 0.3 B |
| Medium | 4.8 A | 0 B | 0 B |
| Large | 4.0 A | 0.3 B | 1.0B |

[a]Means in a row followed by the same letter are not significantly different (alpha = 0.05) using LSD test.

Conclusions:

The data indicates that embodiments of the 2-pack formulation are effective to kill small, medium and large larvae of tropical sod webworms.

The embodiments of the invention in which an exclusive property or privilege is claimed are defined as follows:

1. A method for improving turfgrass health, the method comprising applying to the turfgrass an effective amount of a formulation comprising:
    a paraffinic oil;
    one or more emulsifiers, each of which is independently selected from the group consisting of natural and synthetic alcohol ethoxylates, alcohol alkoxylates, glycerol oleate, and nonyl phenol ethoxylates;
    a pigment;
    a silicone surfactant; and
    water,
    wherein the silicone surfactant represents from about 0.1 wt % to about 5 wt % of the total weight of the paraffinic oil, the one or more emulsifiers, the pigment, and the silicone surfactant;
    wherein the one or more emulsifiers represent from about 0.5 wt % to about 5 wt % of the total weight of the paraffinic oil, the one or more emulsifiers, the pigment, and the silicone surfactant;
    wherein the pigment represents from about 1 wt % to about 10 wt % of the total weight of the paraffinic oil, the one or more emulsifiers, the pigment, and the silicone surfactant; and
    wherein the formulation is an oil-in-water emulsion and the one or more emulsifiers and the silicone surfactant are selected such that the pigment is maintained in dispersion in the oil-in-water emulsion for delivery to the turfgrass.

2. The method of claim 1, wherein the pigment comprises a phthalocyanine.

3. The method of claim 2, wherein the pigment comprises a polychlorinated (Cu II) phthalocyanine.

4. The method of claim 1, wherein the paraffinic oil comprises an isoparaffinic oil.

5. The method of claim 4, wherein the isoparaffinic oil is a synthetic isoparaffinic oil.

6. The method of claim 1, wherein the isoparaffinic oil has an independently selected carbon number distribution of from C16 to C35.

7. The method of claim 1, wherein each of the one or more emulsifiers is independently selected from the group consisting of polyoxyethylene (4 to 7) lauryl ether ($C_{12}$); polyoxyethylene (10) cetyl ether ($C_{16}$), polyoxyethylene (2 to 11) $C_{12}$-$C_{15}$ alcohols, polyoxyethylene (3 to 9) $C_{11}$-$C_{14}$ alcohols, and polyoxyethylene (9) $C_{12}$-$C_{14}$ alcohols.

8. The method of claim 1, wherein each of the one or more emulsifiers is independently selected from the group consisting of natural or synthetic alcohol ethoxylate, glycerol oleate, and nonyl phenol ethoxylates.

9. The method of claim 8, wherein each of the one or more emulsifiers is independently selected from the group consisting of polyoxyethylene (4 to 12) lauryl ether (C12); polyoxyethylene (10) cetyl ether (C16); polyoxyethylene (10) stearyl ether (C18); polyoxyethylene (10) oleyl ether (C18 monounsaturated); polyoxyethylene (2 to 11) C12-C15 alcohols; polyoxyethylene (3 to 9) C11-C14 alcohols; polyoxyethylene (9) C12-C14 alcohols; polyoxyethylene (11) C16-C18 alcohols; polyoxyethylene (20) C12-C15 alcohols, glycerol oleate, and polyoxyethylene (2 to 8) nonylphenol.

10. The method of claim 1, wherein each of the one or more emulsifiers is independently selected from a natural or synthetic alcohol ethoxylate and a glycerol oleate.

11. The method of claim 10, wherein each of the one or more emulsifiers is independently selected from the group consisting of polyoxyethylene (4 to 12) lauryl ether (C12); polyoxyethylene (10) cetyl ether (C16); polyoxyethylene (10) stearyl ether (C18); polyoxyethylene (10) oleyl ether (C18 monounsaturated); polyoxyethylene (2 to 11) C12-C15 alcohols; polyoxyethylene (3 to 9) C11-C14 alcohols; polyoxyethylene (9) C12-C14 alcohols; polyoxyethylene (11) C16-C18 alcohols; polyoxyethylene (20) C12-C15 alcohols, and glycerol oleate.

12. The method of claim 1, wherein the one or more emulsifiers represent from about 1 wt % to about 3 wt % of the total weight of the paraffinic oil, one or more emulsifiers, pigment, and silicone surfactant.

13. The method of claim 1, wherein the one or more emulsifiers represent about 2 wt % of the total weight of the paraffinic oil, one or more emulsifiers, pigment, and silicone surfactant.

14. The method of claim 1, wherein the silicone surfactant comprises polyethylene glycols (PEG) according to Formula (IV):

where: $R_1$=H or $CH_2$=CH—$CH_2$ or $COCH_3$
$R_2$=H or $CH_2$=CH—$CH_2$ or $COCH_3$
n is greater than or equal to 1.

15. The method of claim 1, wherein:
the silicone surfactant is selected from the group consisting of trisiloxanes and silicone polyethers of Formula I

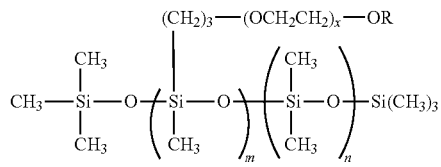

where R=H, $CH_3$, or $COCH_3$; x=1 to 24; n=0 or 1; and m=1.

16. The method of claim 1, wherein
the one or more emulsifiers are selected from the group consisting of polyoxyethylene (4 to 7) lauryl ether ($C_{12}$); polyoxyethylene (10) cetyl ether ($C_{16}$), polyoxyethylene (2 to 11) $C_{12}$-$C_{15}$ alcohols, polyoxyethylene (3 to 9) $C_{11}$-$C_{14}$ alcohols, and polyoxyethylene (9) $C_{12}$-$C_{14}$ alcohols, and
the silicone surfactant comprises polyethylene glycols (PEG) according to Formula (IV):

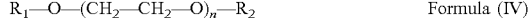

where: $R_1$=H or $CH_2$=CH—$CH_2$ or $COCH_3$
$R_2$=H or $CH_2$=CH—$CH_2$ or $COCH_3$
n is greater than or equal to 1.

17. The method of claim 16, wherein the pigment comprises a polychlorinated (Cu II) phthalocyanine.

18. The method of claim 1, wherein the formulation further comprises one or more chemical fungicides.

19. The method of claim 18, wherein each of the one or more chemical fungicides is independently selected from the group consisting of a demethylation inhibitor, a methyl benzimidazole carbamate, and a dicarboximide.

20. The method of claim 1, wherein the non-aqueous portion of the oil-in-water emulsion is applied to the turfgrass in a range of about 1 gal/acre (0.093 L/100 m²) to about 15 gal/acre (1.395 L/100 m²), a total spray volume of the oil-in-water emulsion being in a range of about 20 gal/acre (1.86 L/100 m²) to about 200 gal/acre (18.6 L/100 m²).

21. The method of claim 1, wherein the non-aqueous portion of the oil-in-water emulsion is applied to the turfgrass in a range of about 1 gal/acre (0.093 L/100 m²) to about 15 gal/acre (1.395 L/100 m²).

22. The method of claim 1, wherein the formulation comprises:
a synthetic isoparaffinic oil having an independently selected carbon number distribution of from C16 to C35;
one or more emulsifiers, each of which is independently selected from the group consisting of natural or synthetic alcohol ethoxylate, glycerol oleate, and nonyl phenol ethoxylates;
a polychlorinated (Cu II) phthalocyanine; and
a silicone surfactant, which is independently selected from the group consisting of trisiloxanes and silicone polyethers of Formula I

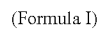

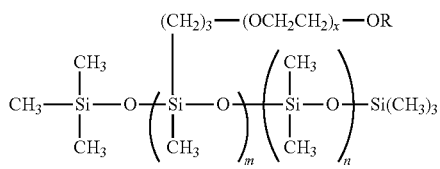

where R=H, $CH_3$, or $COCH_3$; x=1 to 24; n=0 or ≥1; and m=1; and
water;
wherein the silicone surfactant represents from about 0.1 wt % to about 5 wt % of the total weight of the paraffinic oil, one or more emulsifiers, polychlorinated (Cu II) phthalocyanine, and silicone surfactant;
wherein the one or more emulsifiers represent from about 0.5 wt % to about 5 wt % of the total weight of the paraffinic oil, one or more emulsifiers, polychlorinated (Cu II) phthalocyanine, and silicone surfactant;
wherein the polychlorinated (Cu II) phthalocyanine represents from about 1 wt % to about 10 wt % of the total weight of the paraffinic oil, one or more emulsifiers, polychlorinated (Cu II) phthalocyanine, and silicone surfactant; and
wherein the formulation is an oil-in-water emulsion and the one or more emulsifiers and the silicone surfactant are selected such that the polychlorinated (Cu II) phthalocyanines is maintained in dispersion in the oil-in-water emulsion for delivery to the turfgrass.

23. The method of claim 1, wherein the root length of the turfgrass is increased.

24. The method of claim 1, wherein the root mass of the turfgrass is increased.

25. The method of claim 1, wherein the root density of the turfgrass is increased.

26. A method for controlling a turfgrass pest, the method comprising applying to the turfgrass an effective amount of a formulation comprising:
a paraffinic oil;
one or more emulsifiers, each of which is independently selected from the group consisting of natural and synthetic alcohol ethoxylates, alcohol alkoxylates, glycerol oleate, and nonyl phenol ethoxylates;

a pigment;

a silicone surfactant; and water, wherein the silicone surfactant represents from about 0.1 wt % to about 5 wt % of the total weight of the paraffinic oil, the one or more emulsifiers, the pigment, and the silicone surfactant;

wherein the one or more emulsifiers represent from about 0.5 wt % to about 5 wt % of the total weight of the paraffinic oil, the one or more emulsifiers, the pigment, and the silicone surfactant;

wherein the pigment represents from about 1 wt % to about 10 wt % of the total weight of the paraffinic oil, the one or more emulsifiers, the pigment, and the silicone surfactant; and wherein the formulation is an oil-in-water emulsion and the one or more emulsifiers and the silicone surfactant are selected such that the pigment is maintained in dispersion in the oil-in-water emulsion for delivery to the turfgrass.

27. A method for controlling a turfgrass disease due to a fungus, the method comprising applying to the turfgrass an effective amount of a formulation comprising:

a paraffinic oil;

one or more emulsifiers, each of which is independently selected from the group consisting of natural and synthetic alcohol ethoxylates, alcohol alkoxylates, glycerol oleate, and nonyl phenol ethoxylates;

a pigment;

a silicone surfactant; and water, wherein the silicone surfactant represents from about 0.1 wt % to about 5 wt % of the total weight of the paraffinic oil, the one or more emulsifiers, the pigment, and the silicone surfactant;

wherein the one or more emulsifiers represent from about 0.5 wt % to about 5 wt % of the total weight of the paraffinic oil, the one or more emulsifiers, the pigment, and the silicone surfactant;

wherein the pigment represents from about 1 wt % to about 10 wt % of the total weight of the paraffinic oil, the one or more emulsifiers, the pigment, and the silicone surfactant; and wherein the formulation is an oil-in-water emulsion and the one or more emulsifiers and the silicone surfactant are selected such that the pigment is maintained in dispersion in the oil-in-water emulsion for delivery to the turfgrass.

* * * * *

UNITED STATES PATENT AND TRADEMARK OFFICE
CERTIFICATE OF CORRECTION

PATENT NO. : 9,826,738 B2
APPLICATION NO. : 15/272147
DATED : November 28, 2017
INVENTOR(S) : Michael Fefer et al.

It is certified that error appears in the above-identified patent and that said Letters Patent is hereby corrected as shown below:

In the Claims

Column 23, Line 24, Claim 14, delete "$R_1\!=\!H$" and insert -- $R_1=H$ --, therefor.

Column 23, Line 25, Claim 14, delete "$R_2\!=\!H$" and insert -- $R_2=H$ --, therefor.

Column 23, Line 41, Claim 15, delete "$R\!=\!H$," and insert -- $R=H$, --, therefor.

Column 23, Line 41, Claim 15, delete "or 1;" and insert -- or $\geq 1$; --, therefor.

Column 23, Line 54, Claim 16, delete "$R_1\!=\!H$" and insert -- $R_1=H$ --, therefor.

Column 23, Line 55, Claim 16, delete "$R_2\!=\!H$" and insert -- $R_2=H$ --, therefor.

Column 24, Line 33, Claim 22, delete "$R\!=\!H$," and insert -- $R=H$, --, therefor.

Column 24, Lines 51-52, Claim 22, delete "phthalocyanines" and insert -- phthalocyanine --, therefor.

Signed and Sealed this
Third Day of March, 2020

Andrei Iancu
*Director of the United States Patent and Trademark Office*